(12) United States Patent
Ramstad et al.

(10) Patent No.: US 9,839,910 B2
(45) Date of Patent: Dec. 12, 2017

(54) FLUIDIC CARTRIDGES, SYSTEMS, AND METHODS FOR CONDUCTING BIOCHEMICAL REACTIONS

(71) Applicant: Illumina, Inc., San Diego, CA (US)

(72) Inventors: Paul O. Ramstad, San Jose, CA (US); Majid Aghababazadeh, Cupertino, CA (US); Behnam Javanmardi, Saratoga, CA (US)

(73) Assignee: Illumina, Inc., San Diego, CA (US)

( * ) Notice: Subject to any disclaimer, the term of this patent is extended or adjusted under 35 U.S.C. 154(b) by 242 days.

(21) Appl. No.: 14/858,311

(22) Filed: Sep. 18, 2015

(65) Prior Publication Data

US 2016/0089668 A1 Mar. 31, 2016

Related U.S. Application Data

(60) Provisional application No. 62/056,712, filed on Sep. 29, 2014.

(51) Int. Cl.
*B01L 3/00* (2006.01)
*C12Q 1/68* (2006.01)

(52) U.S. Cl.
CPC .............. *B01L 3/502* (2013.01); *B01L 3/523* (2013.01); *C12Q 1/686* (2013.01); *B01L 3/527* (2013.01); *B01L 2200/026* (2013.01); *B01L 2200/028* (2013.01); *B01L 2200/0689* (2013.01); *B01L 2200/16* (2013.01); *B01L 2300/044* (2013.01); *B01L 2300/0672* (2013.01); *C12Q 1/6846* (2013.01)

(58) Field of Classification Search
CPC .. B01L 3/502; B01L 3/523; B01L 2200/0689; B01L 2200/028; B01L 2300/0672; B01L 3/527; B01L 2200/026; B01L 2200/16; B01L 2300/044; C12Q 1/686; C12Q 1/6846

See application file for complete search history.

(56) References Cited

U.S. PATENT DOCUMENTS

2008/0038737 A1* 2/2008 Smith ................ C12Q 1/6848
435/6.12

\* cited by examiner

*Primary Examiner* — Sally A Merkling
(74) *Attorney, Agent, or Firm* — Illumina, Inc.

(57) ABSTRACT

Fluidic cartridge including a liquid container having a reservoir configured to hold a liquid. The liquid container includes an interior surface. The fluidic cartridge also includes a transfer tube that extends from the interior surface to a distal end. The distal end includes a fluidic port that is in flow communication with the reservoir through the transfer tube. The transfer tube has a piercing segment that includes the distal end. The fluidic cartridge also includes a movable seal that is engaged to the piercing segment of the transfer tube and configured to slide along the piercing segment from a closed position to a displaced position during a mating operation. The movable seal blocks flow of the liquid through the fluidic port when in the closed position. The piercing segment extends through the movable seal when in the displaced position.

19 Claims, 8 Drawing Sheets

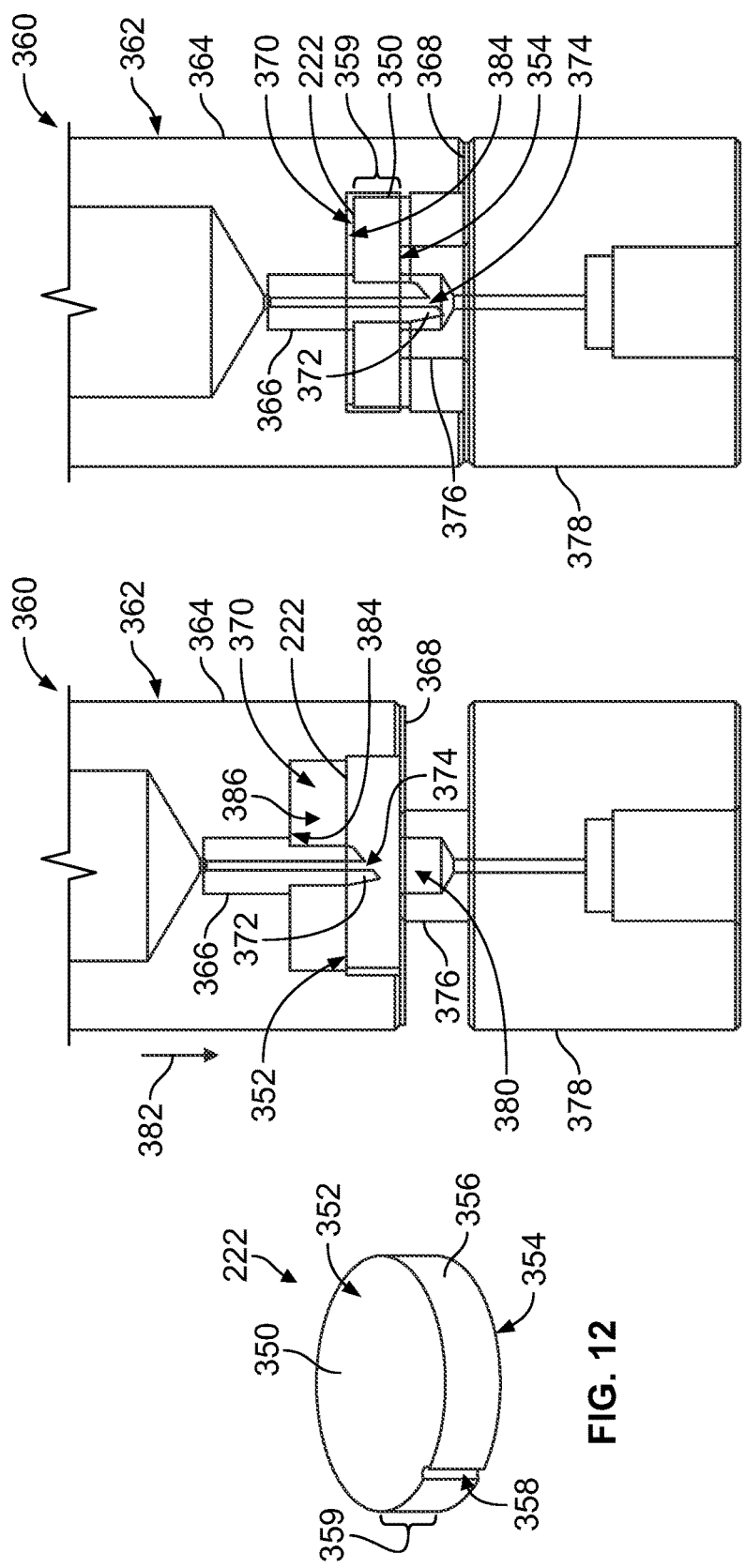

FLUIDIC CARTRIDGES, SYSTEMS, AND METHODS FOR CONDUCTING BIOCHEMICAL REACTIONS

CROSS-REFERENCE TO RELATED APPLICATION

The present application claims the benefit of U.S. Provisional Application No. 62/056,712, which was filed on Sep. 29, 2014 and is incorporated herein by reference in its entirety.

BACKGROUND

Embodiments of the present application relate generally to fluidic cartridges, systems, and methods for conducting biochemical reactions and, more particularly, to systems and methods in which a fluidic cartridge engages a system base to conduct designated reactions for at least one of sample preparation or analysis.

Various biochemical protocols involve performing a large number of controlled reactions on support surfaces or within designated reaction chambers. The controlled reactions may be conducted to analyze a biological sample or to prepare the biological sample for subsequent analysis. The analysis may identify or reveal properties of chemicals involved in the reactions. For example, in an array-based, cyclic sequencing assay (e.g., sequencing-by-synthesis (SBS)), a dense array of DNA features (e.g., template nucleic acids) are sequenced through iterative cycles of enzymatic manipulation. After each cycle, an image may be captured and subsequently analyzed with other images to determine a sequence of the DNA features. In another biochemical assay, an unknown analyte having a detectable label (e.g., fluorescent label) may be exposed to an array of known probes that have predetermined addresses within the array. Observing chemical reactions that occur between the probes and the unknown analyte may help identify or reveal properties of the analyte.

There has been a general demand for systems that automatically perform assays, such as those described above. More recently, there has been a demand for a system that uses pre-packaged components that may be readily added to the system to perform a designated assay. For instance, the above systems may use a large number of solutions (e.g., nucleotides, enzymes, buffers, etc.) while conducting the designated reactions. Cartridges including all or a plurality of the solutions may be shipped to an end user who may then load the cartridge into the system. Such convenience, however, is not without challenges. For instance, the interface between the cartridge and the system may develop unwanted leaks.

In addition, the above systems may include sipper tubes that extend into reservoirs of the cartridge to withdraw the corresponding solutions therefrom. Due to manufacturing tolerances, it may be difficult to position a sipper tube such that all of the solution within the reservoir can be removed. To ensure that a reservoir holds a sufficient amount of the solution for the assay, the reservoir is typically filled to have a volume that is more than necessary. Often, a residual volume (or dead volume) of the solution is not used during the assay and wasted.

Accordingly, a need exists for cartridges that reduce the residual volumes of solutions that are not used during an assay while also providing an interface that does not allow excessive leakage.

BRIEF DESCRIPTION

In an embodiment, a fluidic cartridge is provided that includes a liquid container having a reservoir configured to hold a liquid. The liquid container includes an interior surface. The fluidic cartridge also includes a transfer tube that extends from the interior surface to a distal end. The distal end includes a fluidic port that is in flow communication with the reservoir through the transfer tube. The transfer tube has a piercing segment that includes the distal end. The fluidic cartridge also includes a movable seal that is engaged to the piercing segment of the transfer tube and configured to slide along the piercing segment from a closed position to a displaced position during a mating operation. The movable seal blocks flow of the liquid through the fluidic port when in the closed position. The piercing segment extends through the movable seal when in the displaced position such that the fluidic port clears the movable seal and the liquid is permitted to flow through the fluidic port.

In an embodiment, a method is provided that includes providing a system base configured to receive a liquid for a designated assay. The method also includes providing a fluidic cartridge that includes a transfer tube having a distal end. The distal end includes a fluidic port that is in flow communication with a reservoir of the fluidic cartridge through the transfer tube. The reservoir includes the liquid. The fluidic cartridge also includes a movable seal that is positioned to block flow of the liquid through the fluidic port. The method also includes mating the fluidic cartridge and the system base. The movable seal is displaced by the system base as the fluidic cartridge is mated with the system base such that the movable seal slides along the transfer tube and the fluidic port clears the movable seal, wherein the liquid is permitted to flow through the fluidic port after the fluidic port clears the movable seal.

In an embodiment, a method of assembling a fluidic cartridge is provided. The method includes providing a cartridge housing that has a transfer tube having a distal end. The distal end includes a fluidic port that is in flow communication with a reservoir through the transfer tube. The method also includes positioning a movable seal to block the fluidic port, wherein the movable seal is configured to slide along the transfer tube from a closed position to a displaced position during a mating operation. The movable seal blocks flow of a liquid through the fluidic port when in the closed position. The transfer tube is configured to extend through the movable seal when in the displaced position such that the fluidic port clears the movable seal and the liquid is permitted to flow through the fluidic port.

In an embodiment, a method of re-furbishing a fluidic cartridge is provided. The method includes receiving a fluidic cartridge having a cartridge housing that includes a liquid container and a transfer tube coupled to the liquid container. The transfer tube has a distal end that includes a fluidic port that is in flow communication with a reservoir of the liquid container through the transfer tube. The method also includes removing a used seal that is engaged to the transfer tube and providing a liquid into the reservoir. The method also includes positioning a movable seal to block the fluidic port, wherein the movable seal is configured to slide along the transfer tube from a closed position to a displaced position during a mating operation. The movable seal blocks flow of the liquid through the fluidic port when in the closed position. The transfer tube is configured to extend through the movable seal when in the displaced position such that the fluidic port clears the movable seal and the liquid is permitted to flow through the fluidic port.

In an embodiment, a system is provided that includes a system base configured to conduct an assay protocol with a liquid. The system also includes a fluidic cartridge configured to engage the system base. The fluidic cartridge includes a liquid container having a reservoir configured to hold the liquid. The liquid container includes an interior surface. The fluidic cartridge also includes a transfer tube that extends from the interior surface to a distal end. The distal end includes a fluidic port that is in flow communication with the reservoir through the transfer tube. The transfer tube has a piercing segment that includes the distal end. The fluidic cartridge also includes a movable seal that is engaged to the piercing segment of the transfer tube and configured to slide along the piercing segment from a closed position to a displaced position when the fluidic cartridge is loaded onto the system base. The movable seal blocks flow of the liquid through the fluidic port when in the closed position. The piercing segment extends through the movable seal when in the displaced position such that the fluidic port clears the movable seal and the liquid is permitted to flow through the fluidic port into the system base.

BRIEF DESCRIPTION OF THE DRAWINGS

FIG. 12 is an isolated perspective view of a movable seal in accordance with an embodiment.

FIG. 13 is a cross-section of a fluid-interconnect assembly in accordance with an embodiment that includes the movable seal of FIG. 12.

FIG. 14 is another cross-section of the fluid-interconnect assembly of FIG. 13 after a mating operation with a system base.

DETAILED DESCRIPTION

Embodiments set forth herein include fluid-interconnect assemblies, fluidic cartridges that include the fluid-interconnect assemblies, systems that include the fluidic cartridges, and methods relating to the same. The fluid-interconnect assemblies and fluidic cartridges may include reservoirs that hold a liquid. The reservoirs may be in flow communication with transfer tubes that are operably coupled to movable seals. In some embodiments, the movable seals are configured to move from a closed position to a displaced position to control flow of liquid through the transfer tubes. In the closed position, the movable seal blocks flow through the transfer tube. As the movable seal moves to the displaced position, the transfer tube may pierce through the movable seal. When a fluidic port of the transfer tube clears the movable seal, flow of the liquid is permitted.

Figure 1:
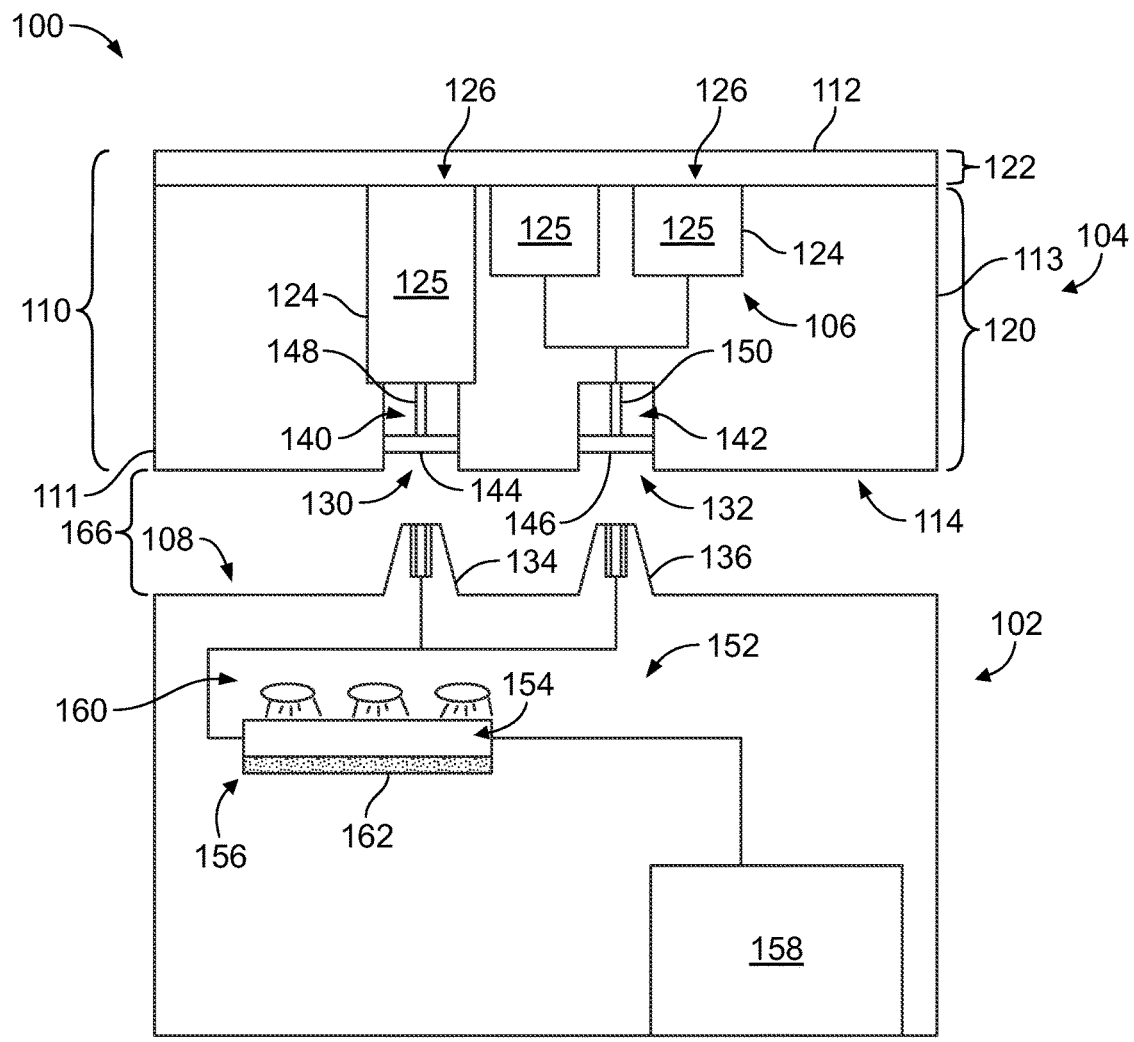
FIG. 1 is a schematic diagram of a system for conducting biological assays in accordance with an embodiment.

Embodiments set forth herein may be used to perform designated reactions for sample preparation and/or biochemical analysis. Although particular embodiments may be used to sequence nucleic acids, it should be understood that other embodiments may be used to perform other protocols or assays. It should also be understood that embodiments could be used in other applications that do not perform biochemical analysis. As used herein, the term "biochemical analysis" may include at least one of biological analysis or chemical analysis. FIG. 1 is a schematic diagram of a system 100 that is configured to conduct biochemical analysis and/or sample preparation. The system 100 includes a system base 102 and a fluidic cartridge 104 that is configured to separably engage the system base 102. In an exemplary embodiment, the system base 102 and the fluidic cartridge 104 are self-contained devices or sub-systems that are configured to operably engage (or mate) with each other so that the system 100 may perform the designated reactions. When operably engaged, the system base 102 and the fluidic cartridge 104 may be mechanically coupled and fluidically coupled and, optionally, electrically and/or optically coupled. The fluidic cartridge 104 may be shipped and/or stored separately with respect to the system base 102 prior to operably engaging each other.

The system base 102 and the fluidic cartridge 104 may be configured to interact with each other to transport a biological sample to different locations within the system 100, to conduct designated reactions that include the biological sample in order to prepare the biological sample for subsequent analysis, and, optionally, to detect one or more events with the biological sample. The events may be indicative of a designated reaction with the biological sample. The fluidic cartridge 104 may be similar to an integrated microfluidic cartridge, such as those shown and described in U.S. Provisional Patent Application No. 62/003,264, filed on May 27, 2014, and/or U.S. Provisional Patent Application No. 62/008,276, filed on Jun. 5, 2014, each of which is incorporated herein by reference in its entirety.

Although the following is with reference to the system base 102 and the fluidic cartridge 104 as shown in FIG. 1, it is understood that the system base 102 and the fluidic cartridge 104 illustrate only one exemplary embodiment of the system 100 and that other embodiments exist. For example, the system base 102 and the fluidic cartridge 104 include various components and features that, collectively, may execute a number of operations for preparing the biological sample and/or analyzing the biological sample. In the illustrated embodiment, each of the system base 102 and the fluidic cartridge 104 are capable of performing certain functions. It is understood, however, that the system base 102 and the fluidic cartridge 104 may perform different functions and/or may share such functions. For example, in the illustrated embodiment, the fluidic cartridge 104 is configured to hold one or more liquids, and the system base 102 is configured to receive the liquids from the fluidic cartridge. In the illustrated embodiment, the system base 102 is a base instrument that is configured to detect designated reactions using liquids from the fluidic cartridge 104. In other embodiments, however, the fluidic cartridge 104 may also be configured to detect the designated reactions. In other embodiments, the system base 102 is a manifold that fluidically interconnects the fluidic cartridge 104 to a base instrument that conducts the designated reactions.

In some embodiments, the fluidic cartridge 104 includes a biological sample. Alternatively, the biological sample may be provided, such as by an end user, to the system 100. As used herein, the biological sample may include one or more biological or chemical substances, such as nucleosides, nucleic acids, polynucleotides, oligonucleotides, proteins, enzymes, polypeptides, antibodies, antigens, ligands, receptors, polysaccharides, carbohydrates, polyphosphates, nanopores, organelles, lipid layers, cells, tissues, organisms, and/or biologically active chemical compound(s), such as analogs or mimetics of the aforementioned species. In some instances, the biological sample may include whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes.

In some embodiments, the biological sample may include an added material, such as water, deionized water, saline solutions, acidic solutions, basic solutions, detergent solutions and/or pH buffers. The added material may also include a biologically active agent, such as a template or digest. The added material may also include reagents that will be used during the designated assay protocol to conduct the biochemical reactions. For example, added liquids may include material to conduct multiple polymerase-chain-reaction (PCR) cycles with the biological sample.

In some embodiments, the system 100 may automatically prepare a sample for biochemical analysis based on a substance provided by the user (e.g., whole blood or saliva). For example, the system 100 may be configured to extract DNA or RNA from a sample and prepare the sample for subsequent analysis. However, in other embodiments, the system 100 may analyze biological samples that are partially or preliminarily prepared for analysis by the user. For example, the user may provide a solution including nucleic acids that were already isolated and/or amplified from whole blood.

As used herein, a "designated reaction" includes a change in at least one of a chemical, electrical, physical, or optical property (or quality) of an analyte-of-interest. In particular embodiments, the designated reaction is an associative binding event (e.g., incorporation of a fluorescently labeled biomolecule with the analyte-of-interest). The designated reaction can be a dissociative binding event (e.g., release of a fluorescently labeled biomolecule from an analyte-of-interest). The designated reaction may be a chemical transformation, chemical change, or chemical interaction. The designated reaction may also be a change in electrical properties. For example, the designated reaction may be a change in ion concentration within a solution. Exemplary reactions include, but are not limited to, chemical reactions such as reduction, oxidation, addition, elimination, rearrangement, esterification, amidation, etherification, cyclization, or substitution; binding interactions in which a first chemical binds to a second chemical; dissociation reactions in which two or more chemicals detach from each other; fluorescence; luminescence; bioluminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding. The designated reaction can also be addition or elimination of a proton, for example, detectable as a change in pH of a surrounding solution or environment. An additional designated reaction can be detecting the flow of ions across a membrane (e.g., natural or synthetic bilayer membrane), for example as ions flow through a membrane the current is disrupted and the disruption can be detected. Field sensing of charged tags can also be used as can thermal sensing and other analytical sensing techniques known in the art.

In particular embodiments, the designated reaction includes the incorporation of a fluorescently-labeled molecule to an analyte. The analyte may be an oligonucleotide and the fluorescently-labeled molecule may be a nucleotide. The designated reaction may be detected when an excitation light is directed toward the oligonucleotide having the labeled nucleotide, and the fluorophore emits a detectable fluorescent signal. In alternative embodiments, the detected fluorescence is a result of chemiluminescence or bioluminescence. A designated reaction may also increase fluorescence (or Förster) resonance energy transfer (FRET), for example, by bringing a donor fluorophore in proximity to an acceptor fluorophore, decrease FRET by separating donor and acceptor fluorophores, increase fluorescence by separating a quencher from a fluorophore or decrease fluorescence by co-locating a quencher and fluorophore.

As used herein, a "reaction component" includes any substance that may be used to obtain a designated reaction. For example, reaction components include reagents, catalysts such as enzymes, reactants for the reaction, samples, products of the reaction, other biomolecules, salts, metal cofactors, chelating agents, and buffer solutions (e.g., hydrogenation buffer). The reaction components may be delivered, individually in liquids or combined in one or more mixture, to various locations in a fluidic network. For instance, a reaction component may be delivered to a reaction chamber where the biological sample is immobilized. The reaction components may interact directly or indirectly with the biological sample. In some embodiments, the fluidic cartridge 104 is pre-loaded with one or more of the reaction components that are necessary for carrying out a designated assay protocol. Preloading can occur at one location (e.g. a manufacturing facility) prior to receipt of the cartridge 104 by a user (e.g. at a customer's facility).

In some embodiments, the system base 102 may be configured to interact with only one fluidic cartridge 104 per session. After the session, the fluidic cartridge 104 may be replaced with another fluidic cartridge 104. In other embodiments, the system base 102 may be configured to interact with more than one fluidic cartridge 104 per session. As used herein, the term "session" includes performing at least one of sample preparation and/or biochemical analysis protocol. Sample preparation may include separating, isolating, modifying and/or amplifying one or more components of the biological sample so that the prepared biological sample is suitable for analysis. In some embodiments, a session may include continuous activity in which a number of controlled reactions are conducted until (a) a designated number of reactions have been conducted, (b) a designated number of events have been detected, (c) a designated period of system time has elapsed, (d) signal-to-noise has dropped to a designated threshold; (e) a target component has been identified; (f) system failure or malfunction has been detected; and/or (g) one or more of the resources for conducting the reactions has depleted. Alternatively, a session may include pausing system activity for a period of time (e.g., minutes, hours, days, weeks) and later completing the session until at least one of (a)-(g) occurs.

An assay protocol may include a sequence of operations for conducting the designated reactions, detecting the designated reactions, and/or analyzing the designated reactions. Collectively, the fluidic cartridge 104 and the system base 102 may include the components that are necessary for executing the different operations. The operations of an assay protocol may include fluidic operations, thermal-control operations, detection operations, and/or mechanical operations.

A "liquid," as used herein, is a substance that is relatively incompressible and has a capacity to flow and to conform to a shape of a container or a channel that holds the substance. A liquid may be aqueous based and include polar molecules exhibiting surface tension that holds the liquid together. A liquid may also include non-polar molecules, such as in an oil-based or non-aqueous substance (e.g., oil). It is understood that references to a liquid in the present application may include a liquid that was formed from the combination of two or more liquids. For example, separate reagent solutions may be later combined to conduct designated reactions. As another example, the liquid may include an aqueous solution and a non-polar liquid (e.g., oil).

In some embodiments, the fluidic cartridge 104 may be used for more than one session while engaged with the system base 102 and/or may be removed from the system base 102, reloaded with reagents, and re-engaged to the system base 102 to conduct additional designated reactions. Accordingly, the fluidic cartridge 104 may be refurbished in some cases such that the same fluidic cartridge 104 may be used with different consumables (e.g., reaction components and/or biological samples). Refurbishing can be carried out at a manufacturing facility after the cartridge has been removed from a system base located at a customer's facility.

The fluidic cartridge 104 may be configured to separably engage or removably couple to the system base 102. For example, in some embodiments, the fluidic cartridge is a disposable cartridge that may be disposed of after a single use. In other embodiments, the fluidic cartridge may be used multiple times during its lifetime. For example, the fluidic cartridge may be reloaded with fluids after a first use and then used again by the same system base or another system base. In some embodiments, the fluidic cartridge may be reloaded with fluids while engaged to the system base 102 or, alternatively, may be reloaded with fluids after being separated from the system base 102. As used herein, when the terms "separably engaged" or "removably coupled" (or the like) are used to describe a relationship between a fluidic cartridge and a system base, the term is intended to mean that a connection between the fluidic cartridge and the system base is readily separable without destroying the system base. Accordingly, the fluidic cartridge may be separably engaged to the system base in a fluidic manner such that the ports of the system base are not destroyed. The fluidic cartridge may be separably engaged to the system base in a mechanical manner such that features of the system base that hold the fluidic cartridge are not destroyed. Optionally, the fluidic cartridge may be separably engaged to the system base in an electrical manner such that the electrical contacts of the system base are not destroyed. The fluidic cartridge is not considered to be "destroyed," for example, if only a simple adjustment to the component (e.g., realigning) or a simple replacement (e.g., replacing a movable seal) is required. For example, the fluidic cartridges may be re-filled after use and have one or more movable seals adjusted and/or replaced. The refurbished fluidic cartridges may then be re-used. In other embodiments, the fluidic cartridge 104 may be permanently coupled to the system base 102 such that the fluidic cartridge 104 is not removed after use. In such embodiments, the fluidic cartridge 104 and the system base 102 may be disposed of after use.

Components (e.g., the fluidic cartridge 104 and the system base 102) may be readily separable when the components can be separated from each other without undue effort or a significant amount of time spent in separating the components. In some embodiments, the fluidic cartridge 104 and the system base 102 may be readily separable without destroying either the fluidic cartridge 104 or the system base 102.

The fluidic cartridge 104 may be operably engaged (or mated) with the system base 102. As used herein, the phrase "operably engaged" and the like include mating the fluidic cartridge to the system base such that the fluidic cartridge and the system base are, at least, fluidically coupled. In some cases, a mating operation (or loading operation) includes inserting the fluidic cartridge into a cavity of the system base in a manner that is similar to inserting a disk or tape into a video player. In other cases, the mating operation may only include connecting the fluidic cartridge to the system base such that the fluidic cartridge and the system base are operably coupled. The mating or loading operation may include mounting the fluidic cartridge onto the system base.

As shown in FIG. 1, the fluidic cartridge 104 includes a fluidic network 106 that may hold and direct fluids (e.g., liquids or gases) therethrough. The fluidic network 106 includes a plurality of interconnected fluidic elements that are capable of storing a fluid and/or permitting a fluid to flow therethrough. Non-limiting examples of fluidic elements include channels, ports of the channels, cavities, storage modules, reservoirs of the storage modules, reaction chambers, waste reservoirs, detection chambers, multipurpose chambers for reaction and detection, and the like. The fluidic elements may be fluidically coupled to one another in a designated manner so that the system 100 is capable of performing sample preparation and/or analysis.

As used herein, the term "fluidically coupled" (or like term) refers to two spatial regions being connected together such that a liquid or gas may be directed between the two spatial regions. In some cases, the fluidic coupling permits a fluid to be directed back and forth between the two spatial regions. In other cases, the fluidic coupling is uni-directional such that there is only one direction of flow between the two spatial regions. For example, an assay reservoir may be fluidically coupled with a channel such that a liquid may be transported into the channel from the assay reservoir. However, in some embodiments, it may not be possible to direct the fluid in the channel back to the assay reservoir. In some embodiments, the fluidic network 106 may be configured to receive a biological sample and direct the biological sample through sample preparation and/or sample analysis.

One or more embodiments may include retaining the biological sample (e.g., template nucleic acid) at a designated location. For example, the biological sample may be retained within the fluidic cartridge 104 or the system base 102. As used herein, the term "retained," when used with respect to a biological sample, includes substantially attaching the biological sample to a surface or confining the biological sample within a designated space. As used herein, the term "immobilized," when used with respect to a biological sample, includes substantially attaching the biological sample to a surface in or on a solid support. Immobilization may include attaching the biological sample at a molecular level to the surface. For example, a biological sample may be immobilized to a surface of a substrate using adsorption techniques including non-covalent interactions (e.g., electrostatic forces, van der Waals, and dehydration of hydrophobic interfaces) and covalent binding techniques where functional groups or linkers facilitate attaching the biological sample to the surface. Immobilizing a biological sample to a surface of a substrate may be based upon the properties of the surface of the substrate, the liquid medium carrying the biological sample, and the properties of the biological sample itself. In some cases, a substrate surface may be functionalized (e.g., chemically or physically modified) to facilitate immobilizing the biological sample to the substrate surface. The substrate surface may be first modified to have functional groups bound to the surface. The functional groups may then bind to the biological sample to immobilize the biological sample thereon. In some cases, a biological sample can be immobilized to a surface via a gel, for example, as described in US Patent Publ. Nos. 2011/0059865 A1 and 2014/0079923 A1, each of which is incorporated herein by reference in its entirety.

In some embodiments, nucleic acids can be immobilized to a surface and amplified using bridge amplification. Useful bridge amplification methods are described, for example, in U.S. Pat. No. 5,641,658; WO 07/010251, U.S. Pat. No. 6,090,592; U.S. Patent Publ. No. 2002/0055100 A1; U.S. Pat. No. 7,115,400; U.S. Patent Publ. No. 2004/0096853 A1; U.S. Patent Publ. No. 2004/0002090 A1; U.S. Patent Publ. No. 2007/0128624 A1; and U.S. Patent Publ. No. 2008/0009420 A1, each of which is incorporated herein in its entirety. Another useful method for amplifying nucleic acids on a surface is rolling circle amplification (RCA), for example, using methods set forth in further detail below. In some embodiments, the nucleic acids can be attached to a surface and amplified using one or more primer pairs. For example, one of the primers can be in solution and the other primer can be immobilized on the surface (e.g., 5'-attached). By way of example, a nucleic acid molecule can hybridize to one of the primers on the surface followed by extension of the immobilized primer to produce a first copy of the nucleic acid. The primer in solution then hybridizes to the first copy of the nucleic acid which can be extended using the first copy of the nucleic acid as a template. Optionally, after the first copy of the nucleic acid is produced, the original nucleic acid molecule can hybridize to a second immobilized primer on the surface and can be extended at the same time or after the primer in solution is extended. In any embodiment, repeated rounds of extension (e.g., amplification) using the immobilized primer and primer in solution provide multiple copies of the nucleic acid. In some embodiments, the biological sample may be confined within a predetermined space with reaction components that are configured to be used during amplification of the biological sample (e.g., PCR).

One or more embodiments set forth herein may be configured to execute an assay protocol that is or includes an amplification (or PCR) protocol. During the amplification protocol, a temperature of the biological sample within a reservoir or channel may be changed in order to amplify the biological sample (e.g., DNA of the biological sample). By way of example, the biological sample may experience (1) a pro-heating stage of about 95° C. for about 75 seconds; (2) a denaturing stage of about 95° C. for about 15 seconds; (3) an annealing-extension stage of about of about 59° C. for about 45 seconds; and (4) a temperature holding stage of about 72° C. for about 60 seconds. Embodiments may execute multiple amplification cycles. It is noted that the above cycle describes only one particular embodiment and that alternative embodiments may include modifications to the amplification protocol.

The methods and systems set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher. The methods and apparatus set forth herein can include detection components or devices having a resolution that is at least sufficient to resolve individual features at one or more of these exemplified densities.

In the illustrated embodiment, the fluidic cartridge 104 includes a cartridge housing 110 having a plurality of housing sides 111-114. The housing sides 111-114 include non-mating sides 111-113 and a mating side 114. The mating side 114 is configured to engage a control side 108 of the system base 102. In the illustrated embodiment, the cartridge housing 110 forms a substantially unitary structure. In alternative embodiments, the cartridge housing 110 may be constructed by one or more sub-components that are combined by a user of the system 100. The sub-components may be combined before the fluidic cartridge 104 is separably engaged to the system base 102 or after one of the sub-components is separably engaged to the system base 102. For example, the cartridge housing 110 may include storage module 120 and a cover or lid 122 that is coupled to the storage module 120. When the cover 122 is removed, one or more containers 124 having reservoirs 125 may be exposed so that liquids may be provided to the reservoirs 125.

The fluidic network 106 is held by the cartridge housing 110 and includes a plurality of the reservoirs 125. The reservoirs 125 form reservoir openings 126 that open to an exterior when the cover 122 is removed. Along the mating side 114, the cartridge housing 110 may include access openings 130, 132. The access openings 130, 132 are sized and shaped relative to base projections (or base plugs) 134, 136, respectively, of the system base 102. The base projections 134, 136 may have respective fluidic ports that are configured to fluidically couple to respective reservoirs 125. The access openings 130, 132 permit the fluidic coupling.

In the illustrated embodiment, the access openings 130, 132 are openings to respective socket chambers 140, 142, respectively. Each of the socket chambers 140, 142 includes a movable seal 144, 146, respectively, and a transfer tube 148, 150, respectively. Each of the transfer tubes 148, 150 may be similar to a needle and configured to pierce through or puncture the respective movable seal. In FIG. 1, the movable seals 144, 146 are coupled to ends of the transfer tubes 148, 150, respectively, thereby closing or blocking flow through fluidic ports of the transfer tubes 148, 150. As described herein, the movable seals 144, 146 are configured to move from a closed position (as shown in FIG. 1) to a displaced position. In the displaced position, the fluidic port of the corresponding transfer tube is no longer blocked or sealed by the movable seal such that liquid may flow therethrough.

The system base 102 may be, for example, a base instrument that conducts and detects the designated reactions. Alternatively, the system base 102 may be a manifold that fluidically interconnects the fluidic cartridge 104 to the base instrument. With respect to FIG. 1, the system base 102 may include a fluidic network 152 that includes the fluidic ports of the base projections 134, 136. The fluidic network 152 may direct liquids from the base projections 134, 136 to operative components of the system base 102. For example, the system base 102 may include a detection chamber 154, a detection assembly 156, a waste reservoir 158, and, optionally, an illumination assembly 160.

The designated reactions may be conducted within the detection chamber 154 and detected by the detection assembly 156. In some embodiments, the detection assembly 156 includes an imaging detector 162. The imaging detector 162 is configured to detect designated reactions within the detection chamber 154. In some embodiments, the imaging detector 162 may be positioned relative to the detection chamber 154 to detect light signals (e.g., absorbance, reflection/refraction, or light emissions) from the detection chamber 154. The imaging detector 162 may include one or more imaging devices, such as a charge-coupled device (CCD) camera or complementary-metal-oxide semiconductor (CMOS) imager. In some embodiments, the imaging detector 162 may detect light signals that are emitted from chemilluminescence. Yet still in other embodiments, the detection assembly 156 may not be limited to imaging applications. For example, the detection assembly 156 may include a sensor (e.g., one or more electrodes) that is configured to detect an electrical property of a liquid.

In particular embodiments, the biological sample may be illuminated by the illumination assembly 160 of the system base 102. For example, the biological sample may include one or more fluorophores that provide light emissions when excited by a light having a suitable wavelength. Alternatively, the illumination assembly 160 may be incorporated with the fluidic cartridge 104.

Collectively, the mating side 114 of the fluidic cartridge 104 and the control side 108 of the system base 102 may define a system interface 166. The system interface 166 represents a common boundary between the fluidic cartridge 104 and the system base 102 through which the system base 102 and the fluidic cartridge 104 are operably engaged. More specifically, the system base 102 and the fluidic cartridge 104 are operably engaged along the system interface 166 such that the system base 102 may control one or more features of the fluidic cartridge 104 through the mating side 114. For instance, the system base 102 may have one or more controllable components that control corresponding components of the fluidic cartridge 104.

In some embodiments, the system base 102 and the fluidic cartridge 104 are operably engaged such that the system base 102 and the fluidic cartridge 104 are secured to each other at the system interface 166 with a fluidic coupling and at least one of an electric coupling, thermal coupling, or optical coupling established through the system interface 166.

In some embodiments, the system base 102 may include a droplet actuator that is capable of manipulating droplets using, for example, electrowetting-mediated operations. In such embodiments, the fluidic cartridge 104 may provide solutions from which the droplets are formed and/or a filler liquid that surrounds the droplets. The filler liquid may be or include, for example, a low-viscosity oil, such as silicone oil or hexadecane filler liquid, and/or a halogenated oil, such as a fluorinated or perfluorinated oil. In some embodiments, the fluidic cartridge 104 is configured to "prime" the droplet actuator by providing a sufficient amount of filler liquid within the droplet actuator for surrounding the droplets.

One example of a droplet actuator is described in U.S. Provisional Application No. 62/008,974, which is incorporated herein by reference in its entirety. As used herein, a "droplet actuator" means a device, system, or assembly that is capable of manipulating droplets. In one or more embodiments, the droplets are manipulated using electrowetting-mediated operations. For examples of droplet actuators, see Pamula et al., U.S. Pat. No. 6,911,132, entitled "Apparatus for Manipulating Droplets by Electrowetting-Based Techniques," issued on Jun. 28, 2005; Pamula et al., U.S. Patent Pub. No. 20060194331, entitled "Apparatuses and Methods for Manipulating Droplets on a Printed Circuit Board," published on Aug. 31, 2006; Pollack et al., International Patent Pub. No. WO/2007/120241, entitled "Droplet-Based Biochemistry," published on Oct. 25, 2007; Shenderov, U.S. Pat. No. 6,773,566, entitled "Electrostatic Actuators for Fluidics and Methods for Using Same," issued on Aug. 10, 2004; Shenderov, U.S. Pat. No. 6,565,727, entitled "Actuators for Fluidics Without Moving Parts," issued on May 20, 2003; Kim et al., U.S. Patent Pub. No. 20030205632, entitled "Electrowetting-driven Micropumping," published on Nov. 6, 2003; Kim et al., U.S. Patent Pub. No. 20060164490, entitled "Method and Apparatus for Promoting the Complete Transfer of Liquid Drops from a Nozzle," published on Jul. 27, 2006; Kim et al., U.S. Patent Pub. No. 20070023292, entitled "Small Object Moving on Printed Circuit Board," published on Feb. 1, 2007; Shah et al., U.S. Patent Pub. No. 20090283407, entitled "Method for Using Magnetic Particles in Droplet Fluidics," published on Nov. 19, 2009; Kim et al., U.S. Patent Pub. No. 20100096266, entitled "Method and Apparatus for Real-time Feedback Control of Electrical Manipulation of Droplets on Chip," published on Apr. 22, 2010; Velev, U.S. Pat. No. 7,547,380, entitled "Droplet Transportation Devices and Methods Having a Liquid Surface," issued on Jun. 16, 2009; Sterling et al., U.S. Pat. No. 7,163,612, entitled "Method, Apparatus and Article for Fluidic Control via Electrowetting, for Chemical, Biochemical and Biological Assays and the Like," issued on Jan. 16, 2007; Becker et al., U.S. Pat. No. 7,641,779, entitled "Method and Apparatus for Programmable Fluidic Processing," issued on Jan. 5, 2010; Becker et al., U.S. Pat. No. 6,977,033, entitled "Method and Apparatus for Programmable Fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, International Patent Pub. No. WO/2009/003184, entitled "Digital Fluidics Based Apparatus for Heat-exchanging Chemical Processes," published on Dec. 31, 2008; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No.

20050179746, entitled "Device for Controlling the Displacement of a Drop Between Two or Several Solid Substrates," published on Aug. 18, 2005; and Dhindsa et al., "Virtual Electrowetting Channels: Electronic Liquid Transport with Continuous Channel Functionality," Lab Chip, 10:832-836 (2010). Each of the above references is incorporated herein by reference in its entirety.

Figure 2:
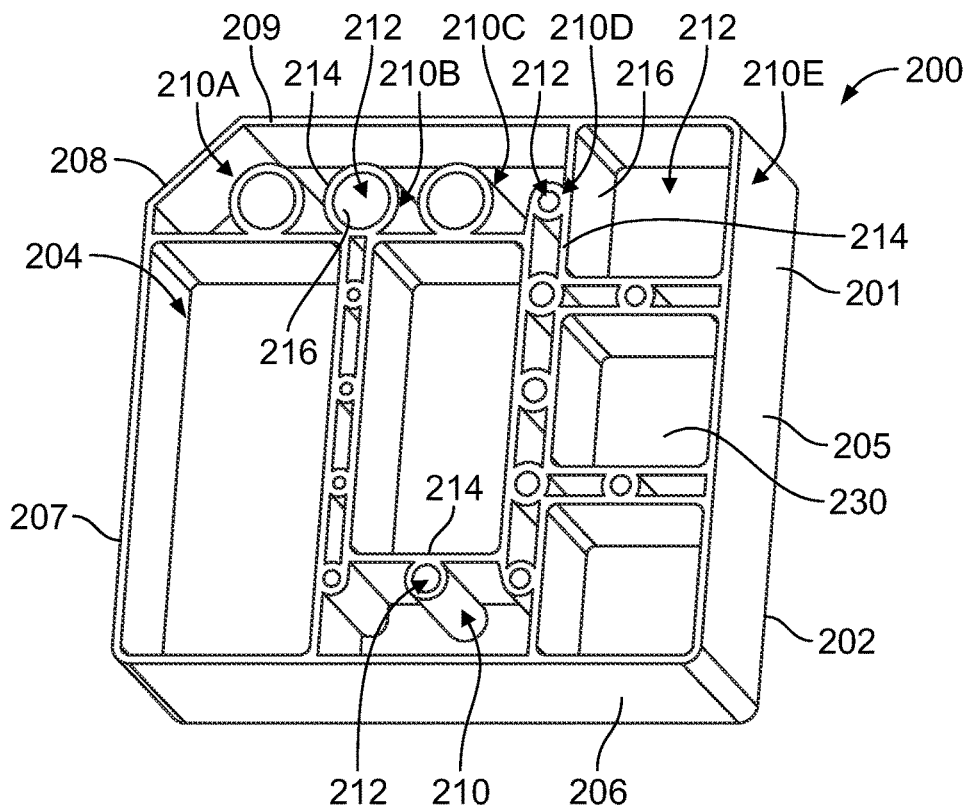
FIG. 2 is an open-sided view of a fluidic cartridge in accordance with an embodiment.
Figure 3:
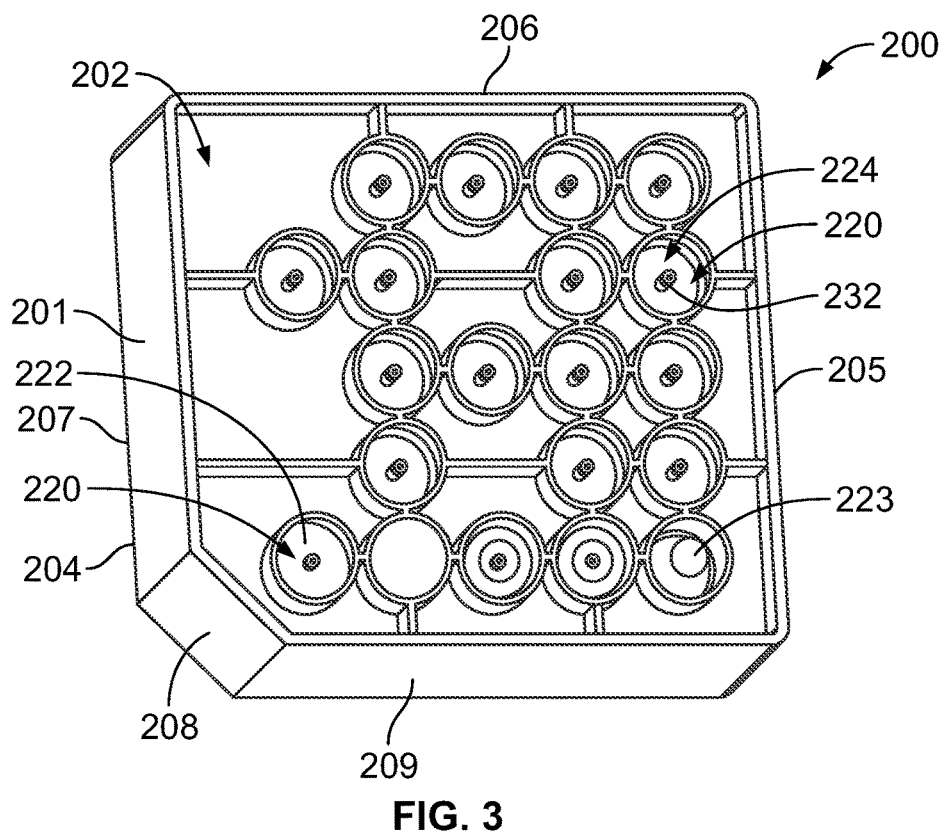
FIG. 3 is a perspective view of a mating side of the fluidic cartridge of FIG. 2.

FIG. 2 is an open-sided view of a fluidic cartridge 200, and FIG. 3 is a perspective view of a mating side 202 of the fluidic cartridge 200. The fluidic cartridge 200 may be similar to the fluidic cartridge 104 (FIG. 1) and be configured to mate with a system base, such as the system base 102 (FIG. 1). The fluidic cartridge 200 includes a cartridge housing 201 having the mating side 202 and a non-mating side 204 that is opposite the mating side 202. The cartridge housing 201 also includes non-mating sides 205-209, which are hereinafter referred to as side walls, that extend between and join the mating side 202 and the non-mating side 204. As shown in FIG. 2, the non-mating side 204 is open to expose a plurality of liquid containers 210, each of which includes a reservoir 212. Each of the reservoirs 212 has at least one outlet port 230. In the illustrated embodiment, the cartridge housing 201 includes twenty (20) liquid containers 210 that each define a corresponding reservoir 212. The cartridge housing 201 may include container walls 214 that form the liquid containers 210. Each of the liquid containers 210 (or the container walls 214) has an interior surface 216 that defines the corresponding reservoir 212.

As shown in FIG. 2, the liquid containers 210 and the corresponding reservoirs 212 may have a variety of sizes and shapes. For example, the liquid containers 210 may have substantially circular or substantially rectangular cross-sections. One or more of the reservoirs 212 may receive a liquid (e.g., solution) that is intended to be used during a designated assay protocol. By way of example, liquid containers 210A-210E are indicated in FIG. 2. Dimensions of the reservoirs 212 may be based on the intended application of the fluidic cartridge 200. For example, the liquid container 210E may hold a washing solution that is used more frequently or extensively than liquids held by the liquid containers 210A-210D. Other liquids may include, for example, a buffer solution, a cleaving solution, or a nucleotides solution. However, other liquids may be used based on the intended assay protocol. After filling the liquids within the corresponding reservoirs 212, a cover (not shown) may be applied to the non-mating side 204 to seal the liquid containers 210 at one end. The cover may be similar to the cover 122 (FIG. 1).

As shown in FIG. 3, the mating side 202 includes a plurality of access openings 220 that provide access to respective movable seals 222, 223. More specifically, the access openings 220 may allow an element of a system base (not shown) to extend through the access openings 220 and engage the corresponding movable seals 222, 223. In the illustrated embodiment, the access openings 220 are openings to socket chambers 224 that are defined by the cartridge housing 201. The socket chambers 224 are in flow communication with corresponding reservoirs 212 (FIG. 2) through flow channels 284 (shown in FIG. 7) that extend between a corresponding outlet port 230 (FIG. 2) within the corresponding reservoir 212 and a corresponding fluidic port 232 within the socket chamber 224. The cartridge housing 201 is configured to hold the movable seals 222, 223 within the corresponding socket chambers 224. Only two (2) of the movable seals 222 and three (3) of the movable seals 223 are shown in FIG. 3. In other embodiments, fewer socket chambers 224 or more socket chambers 224 of the cartridge housing 201 may have a movable seal positioned therein. The movable seals 222, 223 may be positioned to block a flow of the liquids from the reservoirs 212 (FIG. 2) until the movable seals 222, 223 are displaced.

Figure 4:
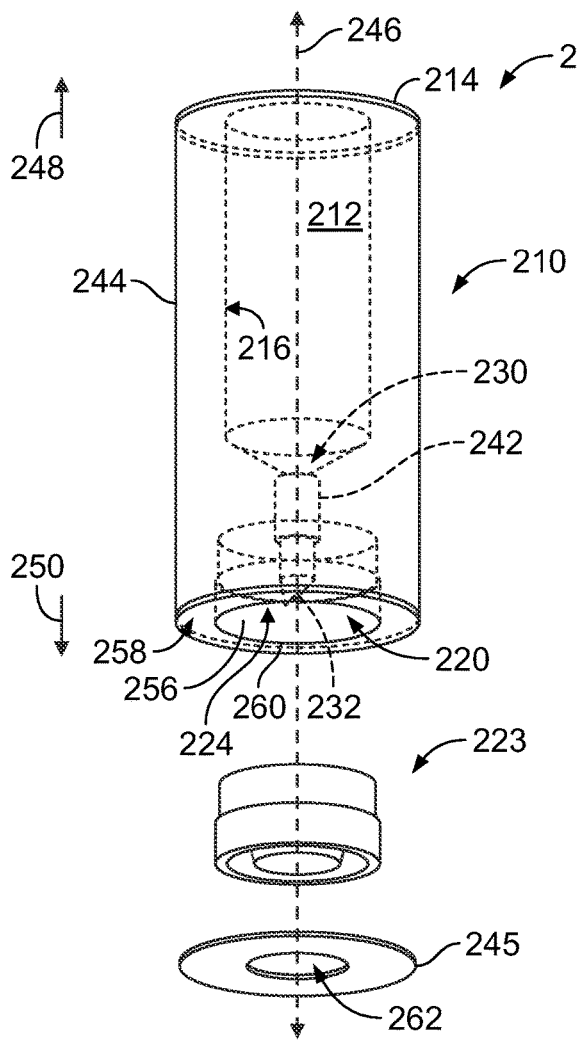
FIG. 4 is an exploded view of a fluid-interconnect assembly that may be used with the fluidic cartridge of FIG. 2.

FIG. 4 is an exploded view of a fluid-interconnect assembly 240 of the fluidic cartridge 200 (FIG. 2). The fluid-interconnect assembly 240 may also be incorporated into the system 100 (FIG. 1). As indicated, portions of the fluid-interconnect assembly 240 are shown in phantom to represent be positioned within or behind another element. The fluid-interconnect assembly 240 includes an exemplary liquid container 210, a transfer tube 242, and an exemplary movable seal 223. Optionally, the fluid-interconnect assembly 240 may also include a retaining element 245.

As described above with respect to FIG. 2, the liquid container 210 may have various dimensions and may be part of the cartridge housing 201 (FIG. 2). In some embodiments, the cartridge housing 201 is a single, continuous piece of material such that the mating side 202 (FIG. 2), the non-mating side 204 (FIG. 2), the side walls 205-209 (FIG. 2), and the liquid containers 210 are formed from a common mold. In other embodiments, the cartridge housing 201 may be assembled from multiple elements. For example, one or more of the walls may be separate or discrete with respect to the liquid containers 210. The container wall 214 of the liquid container 210 may be coupled to, for example, the mating side 202.

The liquid container 210 has a container body 244 that may include the container wall 214. The container wall 214 includes the interior surface 216 that defines the reservoir 212. The container body 244 also defines the socket chamber 224. In the illustrated embodiment, the container body 244 is a single continuous piece of material. In other embodiments, multiple elements may be coupled together to form the container body 244. The container body 244 extends along a central axis 246. In an exemplary embodiment, the central axis 246 extends generally parallel to a force of gravity when the fluidic cartridge 200 (FIG. 1) is in use, such as providing liquids to a system base. However, it is contemplated that other embodiments may not be oriented such that the central axis 246 extends parallel to the force of gravity.

The reservoir 212 opens in a first direction 248 along the central axis 246, and the socket chamber 224 opens in an opposite second direction 250 along the central axis 246. It should be understood, however, the reservoir 212 and the socket chamber 224 are not required to open in opposite directions and may open in different directions in other embodiments. The transfer tube 242 includes the fluidic port 232 and is fluidly coupled to the outlet port 230 of the reservoir 212. Accordingly, the reservoir 212 and the socket chamber 224 are in flow communication with each other through the transfer tube 242.

The transfer tube 242 is needle-shaped and configured to pierce the movable seal 223. The transfer tube 242 may be a non-corroding metal or inert plastic. In the illustrated embodiment, the transfer tube 242 is a discrete element that is coupled to the container body 244. The transfer tube 242 may be molded into the container body 244 (e.g., the container body 244 may be molded or formed around the transfer tube 242), pressed into the container body 244 (e.g., interference fit), screwed into the container body 244, and/or adhered to the container body 244. In other embodiments, the transfer tube 242 may be an integrally molded feature of the container body 244. More specifically, the container body 244 and the transfer tube 242 may be formed from a common mold and constitute a single piece of material.

In some embodiments, the reservoir 212 may be configured to facilitate draining liquid within the reservoir 212 through the outlet port 230 and into the transfer tube 242. For example, the interior surface 216 may define a depression or recess 252 (shown in FIG. 8) having the outlet port 230 located at a bottom of the depression 252. Liquid may collect within the depression 252 when the container body 244 has a designated orientation with respect to gravity. The depression 252 may be shaped such that the liquid does not pool and, instead, drains through the outlet port 230. Compared to conventional systems that use sipper tubes, the depression 252 may reduce an amount of residual volume or "dead volume" within the fluidic cartridge 200.

The container body 244 also has an inner surface 256 that defines the socket chamber 224. The socket chamber 224 may be sized and shaped relative to the movable seal 223. The inner surface 256 may be shaped to engage and hold the movable seal 223 within the socket chamber 224. For example, the inner surface 256 may surround the central axis 246 and have a varying diameter.

The access opening 220 is configured to permit a portion of a system base to be advanced through the access opening 220 so that the system base may engage and move the movable seal 223. After the movable seal 223 is positioned within the socket chamber 224, the retaining element 245 may be coupled to the container body 244. For example, the container body 244 includes an outer surface 258 having an edge 260 that defines the access opening 220. The outer surface 258 may be a portion of the mating side 202 of the fluidic cartridge 200.

In some embodiments, the retaining element 245 may be attached to the outer surface 258 and/or the edge 260. The retaining element 245 is configured to retain or confine the movable seal 223 within the socket chamber 224 while permitting the system base to engage the movable seal 223. For example, the retaining element 245 includes an aperture 262. For embodiments that utilize the retaining element 245, the aperture 262 of the retaining element 245 may define the access opening 220 of the socket chamber 224. The aperture 262 may permit the system base to engage the movable seal 223 while the retaining element 245 prevents the movable seal 223 from being inadvertently removed or withdrawn from the socket chamber 224.

Alternatively or in addition to the retaining element 245, other mechanisms for confining the movable seal 223 within the socket chamber 224 may be used. For example, adhesives may be added to the movable seal and/or one or more surfaces that define the socket chamber 224. Optionally, the adhesives may only be used or activated when the movable seal 223 is in the displaced position. Other mechanisms may be used. For example, the movable seal 223 and the socket chamber 224 may be dimensioned relative to each other to form an interference fit when the movable seal 223 is in the closed position. Also, a circumferential groove may be formed along the inner surface 256 that may permit the movable seal 223 to be positioned within the socket chamber 224, but prevent the movable seal 223 from inadvertently falling out of the socket chamber 224. Similarly, the inner surface 256 may be formed (e.g., heat-staked) to include a wall that has a smaller diameter than the movable seal 223 and prevents the movable seal 223 from inadvertently falling out. Fasteners, such as snap-rings, rivets, and screws, may also be used to confine the movable seal 223 within the socket chamber 224.

Figure 5:
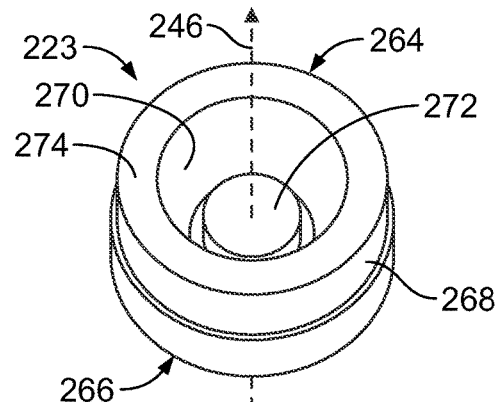
FIG. 5 is a perspective view of a movable seal formed in accordance with an embodiment.
Figure 6:
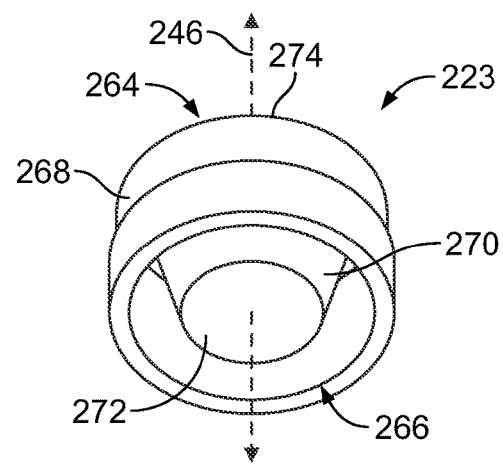
FIG. 6 is another perspective view of the movable seal of FIG. 5.

FIGS. 5 and 6 are isolated perspective views of an exemplary movable seal 223. FIG. 5 illustrates a first or internal side 264, and FIG. 6 illustrates a second or external side 266. The internal side 264 is configured to interface with and/or engage the container body 244 (FIG. 4). The external side 266 is configured to face through the access opening 220 (FIG. 3) and toward an exterior of the fluidic cartridge 200 (FIG. 2). The external side 266 may be exposed to the exterior of the fluidic cartridge 200. The movable seal 223 (or portions thereof) may include an inert compliant material, such as an elastomer (e.g., silicone rubber), that is non-porous. The material may be flexible and/or compressible to facilitate moving the movable seal between different positions and forming a sufficiently leak-proof seal. The material may be capable of being stored in sub-freezing temperatures and used in warmer temperatures.

In the illustrated embodiment, the movable seal 223 includes a securing wall 268, an elastic wall 270, and a seal membrane 272. The securing and elastic walls 268, 270 are joined by a wall rim 274. The seal membrane 272 is configured to directly engage and be pierced by the transfer tube 242 (FIG. 4). The elastic wall 270, the securing wall 268, and the wall rim 274 are configured to cooperate and hold the seal membrane 272 within the socket chamber 224 (FIG. 3).

The securing wall 268 extends around the central axis 246. In the illustrated embodiment, each of the securing wall 268, the elastic wall 270, and the wall rim 274 have circular cross-sections. However, in other embodiments, one or more of the securing wall 268, the elastic wall 270, or the wall rim 274 may not have a circular cross-section. For example, the cross-section may be a polygonal shape (e.g., rectangular) or have a combination of shapes.

Figure 7:
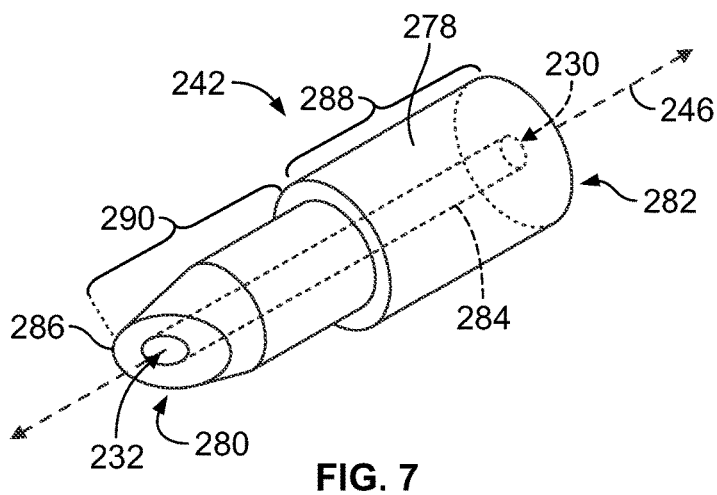
FIG. 7 is an isolated perspective view of a transfer tube that may be used with the fluid-interconnect assembly of FIG. 4.

FIG. 7 is an isolated perspective view of the transfer tube 242. The transfer tube 242 includes a tube body 278. The tube body 278 may be an elongated structure that extends lengthwise along the central axis 246. The tube body 278 extends between a distal (or leading) end 280 and a proximal (or trailing) end 282. The distal end 280 includes the fluidic port 232, and the proximal end 282 includes the outlet port 230. A flow channel 284 of the transfer tube 242 (indicated by dashed lines) extends between the fluidic port 232 and the outlet port 230. The distal end 280 is shaped to pierce the movable seal 223 (FIG. 4) or, more specifically, the seal membrane 272 (FIG. 5). For example, the distal end 280 may include a pointed tip 286 that is capable of piercing the movable seal 223.

The tube body 278 may be sized and shaped relative to a coupling passage 292 (shown in FIG. 8) defined by the container body 244 (FIG. 4). As shown, the tube body 278 may include a coupling segment 288 and a piercing segment 290. The coupling segment 288 may represent the portion of the tube body 278 that couples to the container body 244. For example, the coupling segment 288 of the tube body 278 may be sized and shaped to form an interference fit with an interior surface of the container body 244. In some embodiments, the coupling segment 288 may include external threads for screwing the coupling segment 288 into the container body 244. Alternatively, the transfer tube 242 may be integrally formed with the container body 244 as described herein.

The piercing segment 290 may represent the portion of the tube body 278 that extends into the socket chamber 224 (FIG. 3). The piercing segment 290 may directly engage and physically pierce through the movable seal 223. To this end, the piercing segment 290 may be shaped to facilitate piercing the movable seal 223. In FIG. 7, the coupling segment 288 and the piercing segment 290 have different diameters measured across the central axis 246. In other embodiments, however, the diameters may be equal. In other words, the tube body 278 may have a uniform diameter from the distal end 280 to the proximal end 282.

Figure 8:
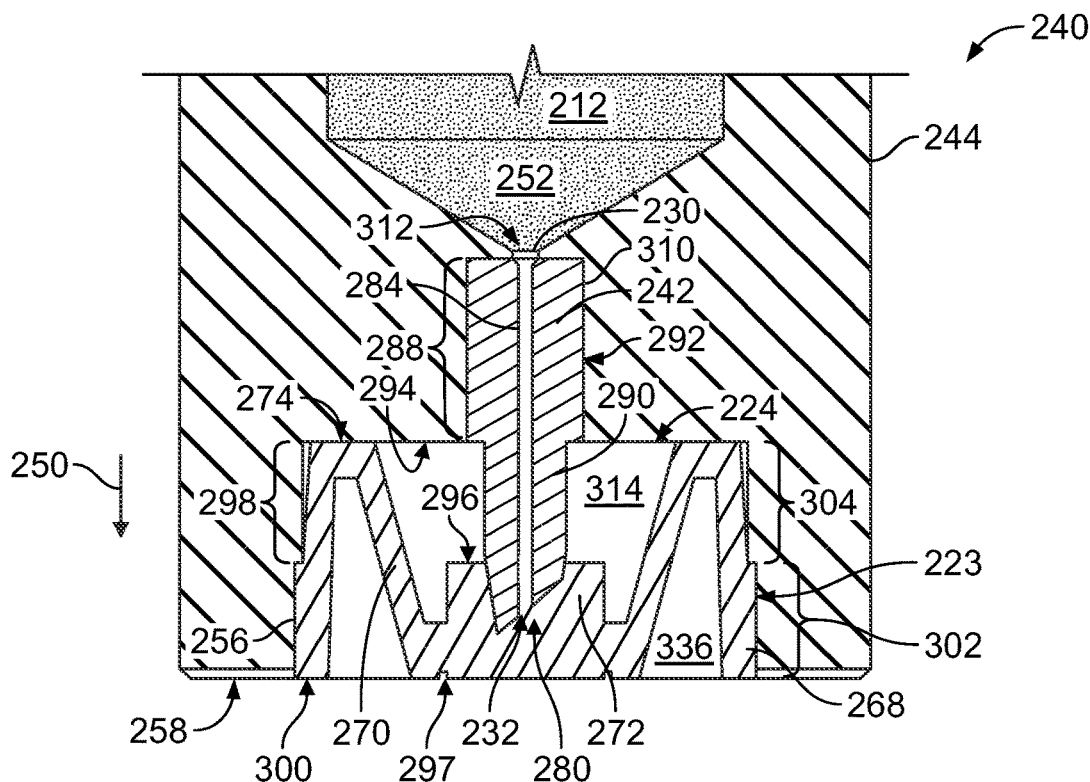
FIG. 8 is an enlarged cross-section of the fluid-interconnect assembly when fully constructed.

FIG. 8 is an enlarged cross-section of a portion of the fluid-interconnect assembly 240. As shown, the movable seal 223 is disposed within the socket chamber 224 of the container body 244. The coupling segment 288 of the transfer tube 242 is secured to the container body 244 and the piercing segment 290 extends into the socket chamber 224. The coupling segment 288 is directly engaged to a corresponding passage surface 310 of the container body 244 that defines the coupling passage 292. The outlet port 230 of the transfer tube 242 is aligned and fluidly coupled to a reservoir port 312 of the container body 244. The reservoir port 312 is located within the depression 252 of the reservoir 212. During operation, liquid within the depression 252 may flow through the reservoir port 312 and the outlet port 230 and into the flow channel 284.

The socket chamber 224 is partially defined by an interior surface 294 that faces in the second direction 250. The piercing segment 290 extends from the interior surface 294 to the distal end 280. In FIG. 8, the movable seal 223 is in a closed position. In the closed position, the fluidic port 232 of the transfer tube 242 is blocked or closed off by the movable seal 223 such that liquid is not permitted to flow through the fluidic port 232. In the illustrated embodiment, the distal end 280 is embedded within the seal membrane 272 of the movable seal 223 such that the fluidic port 232 is blocked. In other embodiments, the distal end 280 may not be embedded within the seal membrane 272. Instead, the distal end 280 may be pressed against the seal membrane 272, without piercing the movable seal 223, such that the fluidic port 232 is blocked.

When the movable seal 223 is positioned within the socket chamber 224, an operative cavity 314 of the socket chamber 224 may be defined between the interior surface 294 and the movable seal 223 or, more specifically, surfaces of the movable seal 223. The surface of the movable seal 223 may extend along the seal membrane 272 and the elastic wall 270. For example, the seal membrane 272 may include an inner side surface 296 that faces the interior surface 294 of the container body 244. A displaced distance or gap 298 measured along the central axis 246 (FIG. 4) exists between the interior surface 294 and the inner side surface 296. The displaced distance 298 may represent an amount of displacement that may occur to the seal membrane 272 during the mating operation. Also shown in FIG. 8, the socket chamber 224 includes a radial space 336 that is located between the elastic wall 270 and the securing wall 268. The radial space 336 is sized to permit the elastic wall 270 to flex into the radial space 336 during the mating operation.

When the movable seal 223 is in the closed position, the distal end 280 extends through (e.g., pierces through) the inner side surface 296. However, the fluidic port 232 does not clear an outer side surface 297 of the seal membrane 272 when the seal membrane 272 is in the closed position. The outer side surface 297 faces the access opening 220 and may be exposed to an exterior of the cartridge housing 201. Instead, the distal end 280 is embedded within a thickness of the seal membrane 272.

In the illustrated embodiment, the movable seal 223 may be substantially flush with the outer surface 258. For example, the securing wall 268 of the movable seal 223 includes a rim edge 300. The rim edge 300 and the outer side surface 297 of the seal membrane 272 may be substantially flush with the outer surface 258 (or coplanar with the outer surface 258). Alternatively, the rim edge 300 and/or the outer side surface 297 may be located a depth within the socket chamber 224. Alternatively, the rim edge 300 and/or the outer side surface 297 may project a distance beyond the outer surface 258.

The securing wall 268 extends along the inner surface 256 from the rim edge 300 to the wall rim 274. The securing wall 268 may directly interface with the inner surface 256. In some embodiments, the securing wall 268 is shaped relative to the inner surface 256 such that the securing wall 268 has similar dimensions as the socket chamber 224. For example, the inner surface 256 may have a stepped configuration such that the inner surface 256 defines a first cavity portion 302 and a second cavity portion 304. The first cavity portion 302 is located proximate to the outer surface 258 or the exterior of the fluidic cartridge 200 (FIG. 1). The second cavity portion 304 is located proximate to the interior surface 294. Each of the first cavity portion 302 and the second cavity portion 304 has a respective chamber diameter measured transverse to the central axis 246 (FIG. 4). The diameter of the first cavity portion 302 is greater than the diameter of the second cavity portion 304. In a similar manner, the securing wall 268 may be sized and shaped to have different outer diameters that are similar to the chamber diameters of the first and second cavity portions 302, 304.

The wall rim 274 engages the interior surface 294 and extends radially between the securing wall 268 and the elastic wall 270. Each of the securing wall 268, the elastic wall 270, and the wall rim 274 surround the central axis 246. In FIG. 8, the elastic wall 270 is in a first condition. In the first condition, the seal membrane 272 is held in the closed position with respect to the transfer tube 242. As described in greater detail below, the elastic wall 270 is configured to flex (e.g., compress or bend) to permit the seal membrane 272 to be displaced and moved toward the interior surface 294. The seal membrane 272 may be displaced such that the fluidic port 232 clears the outer side surface 297 of the seal membrane 272. As the seal membrane 272 is displaced, the inner side surface 296 may move closer to the interior surface 294 thereby reducing a size of the operative cavity 314.

Figure 9:
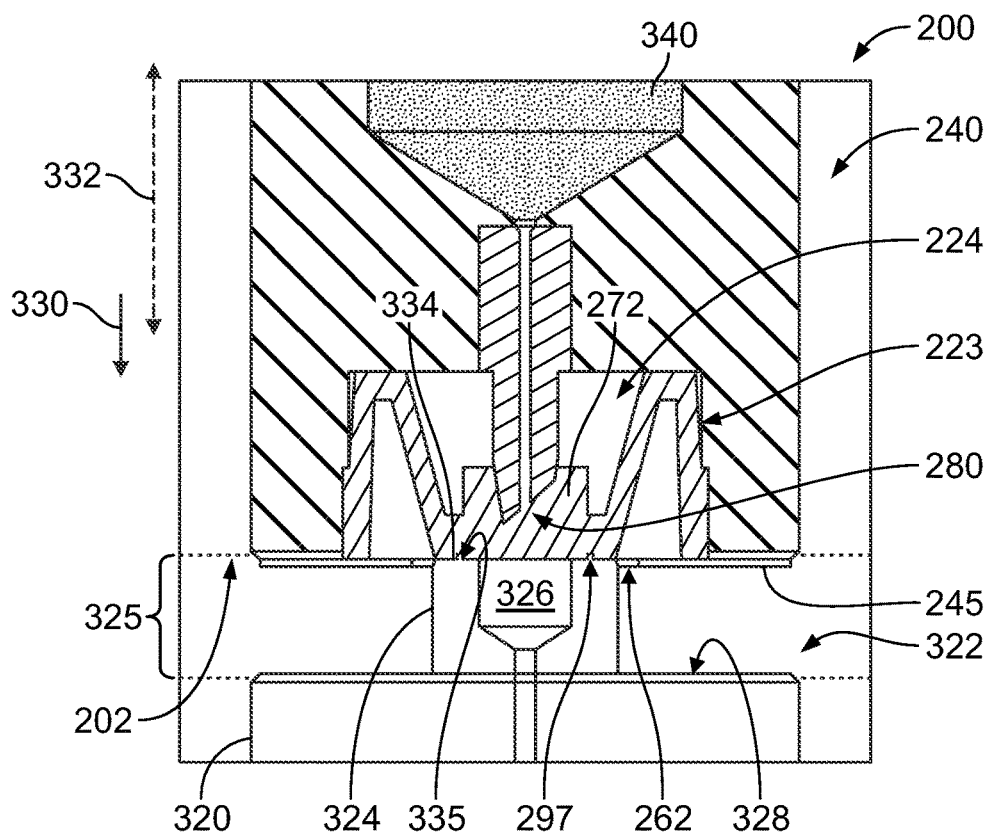
FIG. 9 illustrates an alignment stage of a mating operation between a portion of the fluidic cartridge of FIG. 2 and a portion of the system base.
Figure 10:
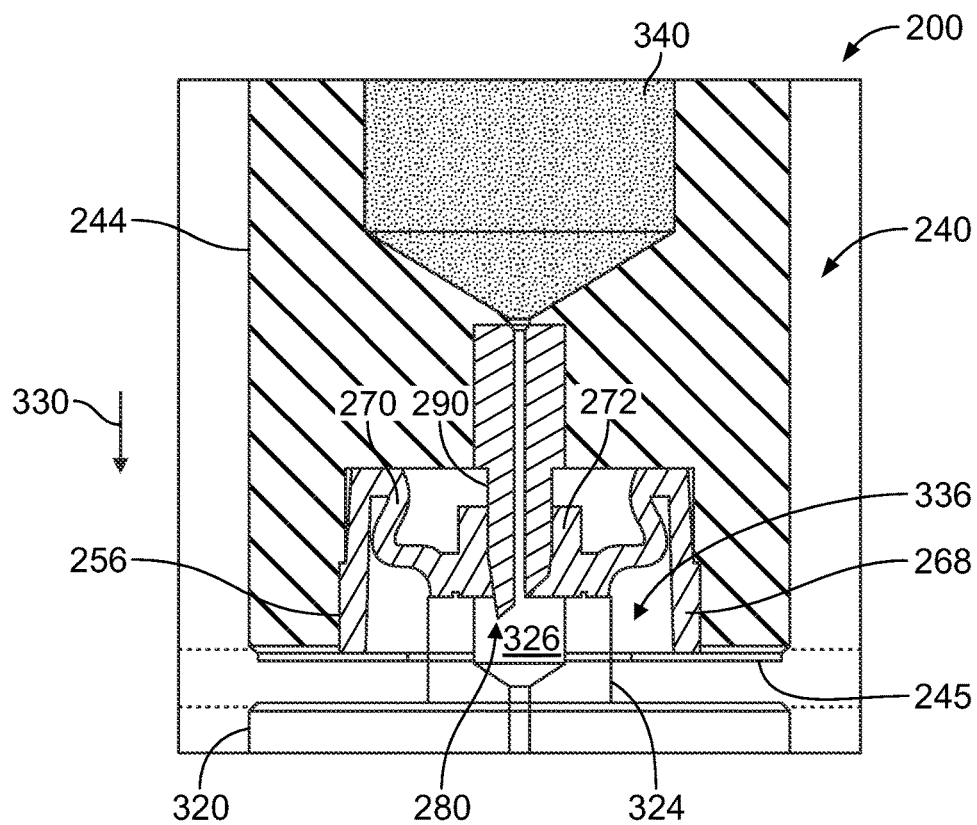
FIG. 10 illustrates movement of the movable seal of FIG. 5 between a closed position and a displaced position during the mating operation.
Figure 11:
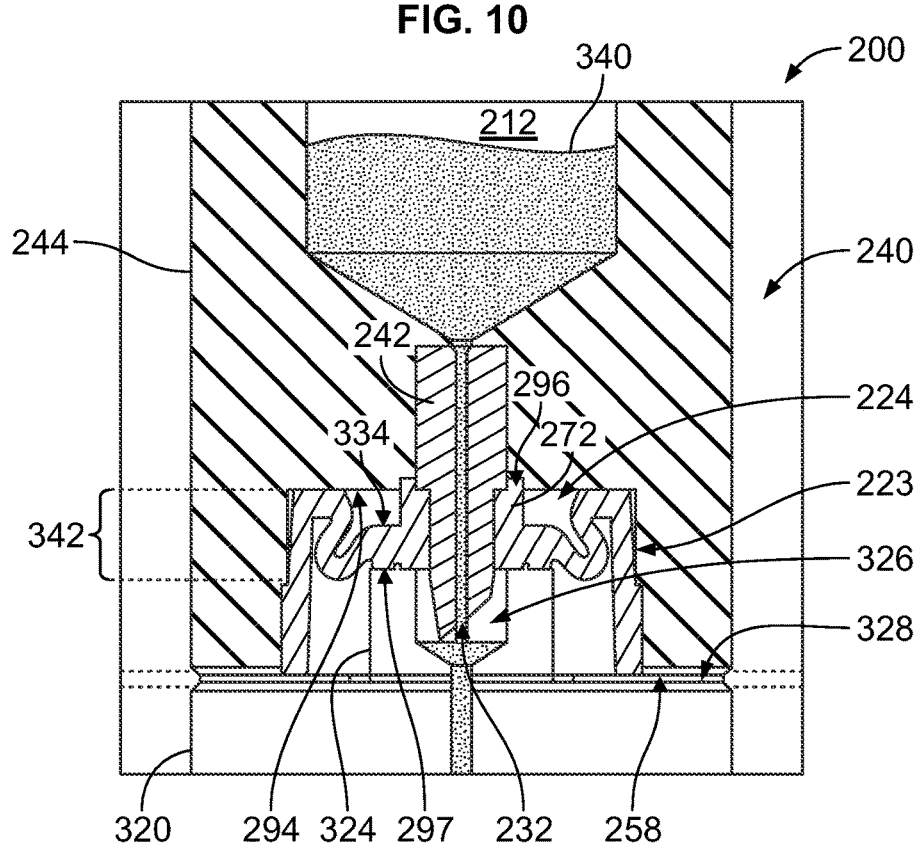
FIG. 11 illustrates the movable seal in the displaced position when the fluidic cartridge of FIG. 2 and the system base are fully mated.

FIGS. 9-11 illustrate a portion of the fluidic cartridge 200 during a mating operation with a system base 320. Although the following description is with particular reference to a single fluidic-interconnect assembly 240, it should be understood that the description is also applicable to the fluidic cartridge 200 as a whole having a plurality of the fluid-interconnect assemblies 240. With respect to FIG. 9, the system base 320 includes a control side 322 having a base projection 324 that extends away from a surface 328 of the control side 322. The base projection 324 may also be referred to as a base plug. The base projection 324 includes a fluidic port 326 that is configured to receive the distal end 280 of the transfer tube 242 during the mating operation. The base projection 324 is dimensioned to pass through the aperture 262 of the retaining element 245. As shown, the base projection 324 extends a height 325 from the surface 328. The height 325 may be configured relative to a desired displacement distance of the movable seal 223 and to achieve a desired compression of the movable seal 223 after the mating operation.

In FIG. 9, the movable seal 223 is in the closed position with the seal membrane 272 positioned proximate to an exterior of the fluidic cartridge 200. To mate the system base 320 and the fluidic cartridge 200, the mating side 202 of the fluidic cartridge 200 may be positioned such that the socket chamber 224 is aligned with the base projection 324 of the system base 320. During this alignment stage, the base projection 324 may extend through the aperture 262 of the retaining element 245 and engage or interface with the movable seal 223. More specifically, a port surface 334 of the base projection 324 may engage or interface with the outer side surface 297 of the seal membrane 272. The fluidic port 326 of the base projection 324 opens to the port surface 334. In some embodiments, the port surface 334 may include a circumferential ridge 335 that surrounds the fluidic port 326. The circumferential ridge 335 may facilitate sealing the fluidic connection and preventing leakage of liquid 340.

Once the fluidic cartridge 200 is sufficiently aligned with respect to the system base 320, the fluidic cartridge 200 may be moved toward the system base 320 in a loading direction 330 along a loading axis 332. In particular embodiments, the loading axis 332 extends parallel to a gravitational force axis. Accordingly, the mating side 202 of the fluidic cartridge 200 may face in a downward direction that is parallel to the gravitational force axis. The mating side 202 may be pushed down onto the control side 322. In such embodiments, the control side 322 of the system base 320 may represent a top side of the system base 320. The system base 320 may effectively support the fluidic cartridge 200 after the mating operation.

Optionally, one or more additional elements may be used to facilitate aligning the fluidic cartridge 200 with the system base 320. For example, the fluidic cartridge 200 and the system base 320 may include complementary alignment features (e.g., pins and holes, ribs and grooves, etc.) that may be used to ensure alignment between the fluidic cartridge 200 with the system base 320.

Turning to FIG. 10, as the container body 244 moves toward the system base 320 in the loading direction 330, the base projection 324 engages the seal membrane 272 and prevents the seal membrane 272 from moving in the loading direction 330. Due to the force of the mating operation, the elastic wall 270 may flex (e.g., bend and/or compress) thereby allowing the movable seal 223 to move from the closed position to a displaced position that is closer to the container body 244. In particular embodiments, the elastic wall 270 may flex (e.g., buckle) radially outward such that the elastic wall 270 is flexed into the radial space 336. As the container body 244 and the base projection 324 move closer to each other, the piercing segment 290 pierces through the seal membrane 272 and the distal end 280 is received within the fluidic port 326 of the system base 320. During the mating operation, the securing wall 268 may remain substantially stationary or fixed relative to the container body 244 or the inner surface 256.

FIG. 11 shows the movable seal 223 in a final displaced position. Although not shown, a locking mechanism (e.g., clamp) may be used to maintain the engagement between the fluidic cartridge 200 and the system base 320 throughout operation. As shown, the outer surface 258 of the container body 244 or the retaining element 245 may interface with the surface 328 of the system base 320. In the final displaced position, the fluidic port 232 has cleared the seal membrane 272 such that the liquid 340 is permitted to flow through the fluidic port 232 of the transfer tube 242 and into the fluidic port 326 of the system base 320. As shown, the base projection 324 is positioned within the socket chamber 224. In some embodiments, the seal membrane 272 may be compressed between the port surface 334 of the base projection 324 and the interior surface 294 of the container body 244. As shown, a thickness 342 of the seal membrane 272 is measured between the inner side surface 296 and the outer side surface 297. The thickness 342 may be configured relative to a length of the piercing segment 290 so that the fluidic port 232 may clear the outer side surface 297 and advance into the fluidic port 326.

The seal membrane 272 may be compressed between the base projection 324 and the container body 244 such that a sufficiently leak-proof fluidic connection is established. More specifically, the seal membrane 272 may be sufficiently elastic or compressible such that the seal membrane 272 seals possible gaps between the port surface 334 and the outer side surface 297 of the seal membrane 272. As such, when the liquid 340 flows through the transfer tube 242 and into the fluidic port 326, the liquid 340 does not leak through the interface between the port surface 334 and the outer side surface 297 of the seal membrane 272.

Although not shown in FIG. 11, the fluidic cartridge 200 and/or the system base 320 may have one or more features or elements that facilitate flowing the liquid 340 from the reservoir 212 to the system base 320. For example, the fluidic cartridge 200 and/or the system base 320 may include one or more pumps that drive the liquid 340 through the transfer tube 242. The pumps may be upstream or downstream with respect to the transfer tube 242. In some embodiments, the reservoir 212 may be vented to enable full transfer of the liquid 340. For example, a vent or hole may be provide within the cover (not shown) of the fluidic cartridge 200. In some cases, a top foil may seal an open end of the reservoir 212. When flow of the liquid 340 is desired, the foil may be pierced or removed. Alternatively, a hydrophobic porous frit or a duck-bill valve may be used to allow air into the reservoir 212.

FIG. 12 is an isolated perspective view of the movable seal 222 in accordance with an embodiment, which may be used with the fluidic cartridge 200 (FIG. 2) and may be incorporated with a fluid-interconnect assembly 360 (shown in FIG. 14). The movable seal 222 may be similar to the movable seal 223 (FIG. 3). For example, the movable seal 222 may include an inert compliant material, such as silicone rubber, that is non-porous. The material may be flexible and/or compressible to facilitate moving the movable seal between different positions and forming a sufficiently leak-proof seal. The material may be capable of being stored in sub-freezing temperatures and used in warmer temperatures.

The movable seal 222 may constitute a seal membrane 350 that is similar to the seal membrane 272 (FIG. 5). The seal membrane 350 has an inner side surface 352 and an outer side surface 354. The inner side surface 352 is configured to face an interior of the fluid-interconnect assembly 360, and the outer side surface 354 is configured to engage a system base. In other embodiments, however, the seal membrane 350 may be inverted such that the side surface 352 is the outer side surface and the side surface 354 is the inner side surface.

The seal membrane 350 has a seal edge 356 that extends between the inner side surface 352 and the outer side surface 354 and defines a profile of the seal membrane 350. In the illustrated embodiment, the seal membrane 350 is substantially disc-shaped. However, the seal membrane 350 may have other profiles. For example, the seal membrane 350 may be triangular, rectangular, or other polygonal shape (e.g., pentagon, hexagon, etc.). In some embodiments, the seal edge 356 may be partially curved and partially linear to form, for example, a semi-circle. The profile of the seal membrane 350 may be based on, for example, a shape of the corresponding socket chamber. Likewise, the seal membrane 272 (FIG. 5) may have other profiles. As shown, the seal membrane 350 has a substantially uniform thickness 359 measured between the inner side surface 352 and the outer side surface 354. Alternatively, the thickness 359 may not be uniform. For example, the seal membrane 350 may be similar to the seal membrane 272 and include a raised level having a smaller diameter than the base level.

As shown, the seal edge 356 includes a passage 358 that extends from the inner side surface 352 to the outer side surface 354. The passage 358 is open-sided along the seal edge 356 and is configured to vent air within the socket chamber to allow the movable seal 222 to be moved to a displaced position. Alternatively, the passage 358 may not be located along the seal edge 356 and, instead, extend through the seal membrane 350. In such embodiments, the passage 358 may be positioned with respect to the transfer tube and fluidic ports to reduce the likelihood of leakage.

FIGS. 13 and 14 show cross-sections of the fluid-interconnect assembly 360, which may be incorporated into fluidic cartridges, such as the fluidic cartridge 200. The fluid-interconnect assembly 360 may include similar or identical elements as the fluid-interconnect assembly 240 (FIG. 4). For example, the fluid-interconnect assembly 360 includes a liquid container 362 having a container body 364, a transfer tube 366 that is coupled to the container body 364, and a retaining element 368 that is coupled to the container body 364. The container body 364 defines a socket chamber 370 having the transfer tube 366 and the movable seal 222 disposed therein. The transfer tube 366 includes a distal end 372 having a fluidic port 374. In some embodiments, the container body 364, the transfer tube 366, and the retaining element 368 may be identical to the container body 244 (FIG. 4), the transfer tube 242 (FIG. 4), and the retaining element 245 (FIG. 4), respectively. However, the movable seal 222 has a different shape than the movable seal 223.

FIG. 13 shows the fluid-interconnect assembly 360 when the movable seal 222 is initially aligned with a base projection 376 of a system base 378. The base projection 376 includes a fluidic port 380 (FIG. 13) that is configured to receive the distal end 372 of the transfer tube 366 during the mating operation. The movable seal 222 is in a closed position in FIG. 13. Once the movable seal 222 is sufficiently aligned with respect to the base projection 376, the container body 364 may be moved toward the system base 378 in a loading direction 382.

FIG. 14 shows the movable seal 222 in a final displaced position. In the final displaced position, the fluidic port 374 of the distal end 372 has cleared the seal membrane 350 such that liquid is permitted to flow through the fluidic port 374 of the transfer tube 366 and into the fluidic port 380 of the system base 378. As shown, the base projection 376 is positioned within the socket chamber 370. The seal membrane 350 may be compressed between the base projection 376 and an interior surface 384 of the container body 364. The thickness 359 may be configured relative to a length of the transfer tube 366 so that the fluidic port 374 clears the outer side surface 354 and advances into the fluidic port 380. Like the seal membrane 272 (FIG. 5), the seal membrane 350 may be compressed between the base projection 376 and the container body 364 such that a sufficiently leak-proof fluidic connection is established.

As the movable seal 222 moves from the closed position (FIG. 13) to the displaced position (FIG. 14) air within the socket chamber 370 may be displaced by the movable seal 222 and driven through the passage 358 (FIG. 12). More specifically, an operative cavity 386 (FIG. 13) may be defined between the inner side surface 352 and the interior surface 384 of the container body 364. The operative cavity 386 may reduce in volume as the movable seal 222 moves toward the interior surface 384.

Figure 15:
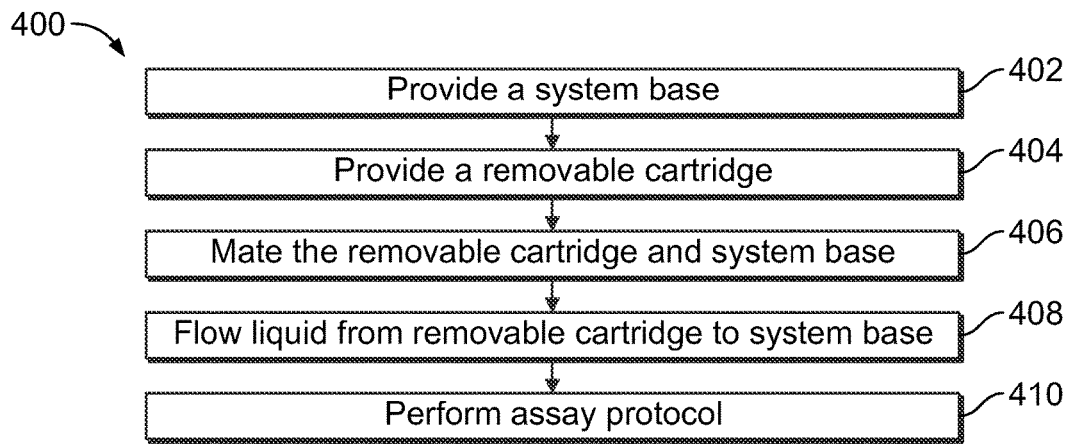
FIG. 15 is a block diagram illustrating a method of mating a fluidic cartridge to a system base in accordance with an embodiment.
Figure 16:
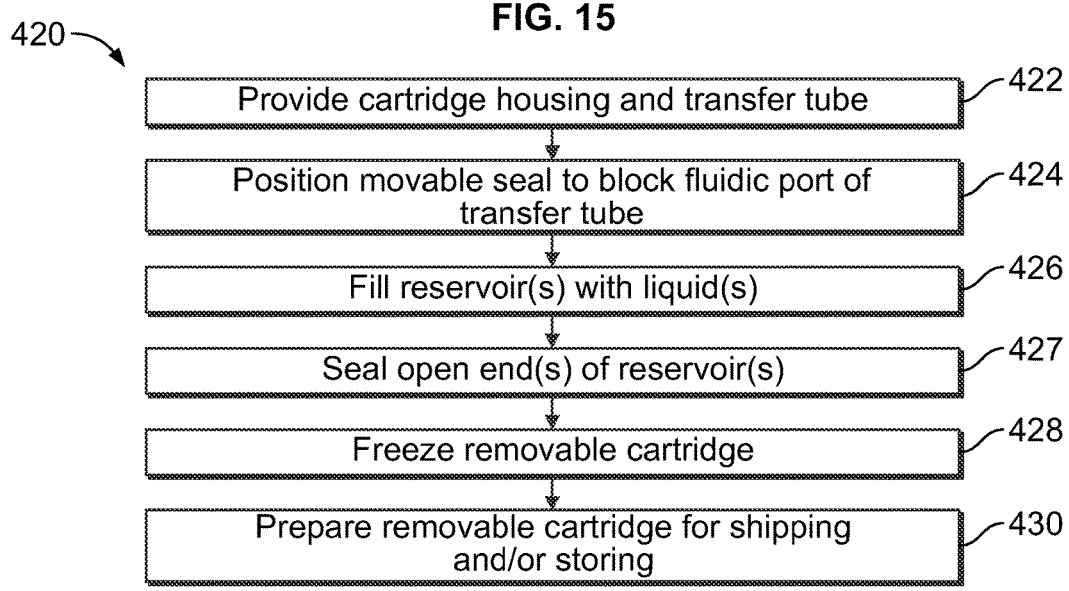
FIG. 16 is a block diagram illustrating a method of assembling a fluidic cartridge in accordance with an embodiment.
Figure 17:
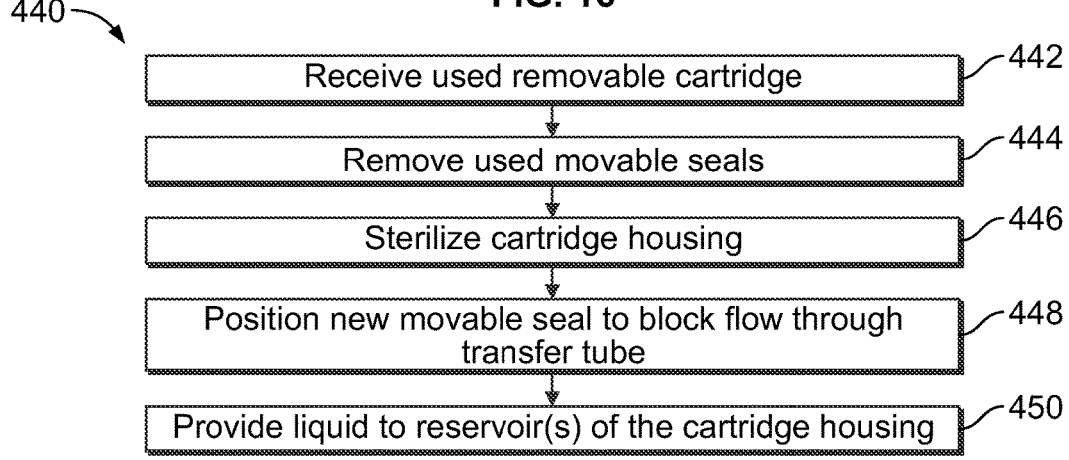
FIG. 17 is a block diagram illustrating a method of re-furbishing a used fluidic cartridge in accordance with an embodiment.

FIGS. 15-17 illustrate various methods in accordance with some embodiments. At least some of the methods are illustrated in the figures as a plurality of steps. However, it should be understood that embodiments are not limited to the steps illustrated in the figures. Steps may be omitted, steps may be modified, and/or other steps may be added. Moreover, steps described herein may be combined, steps may be performed simultaneously, steps may be performed concurrently, steps may be split into multiple sub-steps, steps may be performed in a different order, or steps (or a series of steps) may be re-performed in an iterative fashion. In addition, although different methods are set forth herein, it should be understood that the different methods (or steps of the different methods) may be combined in other embodiments.

FIG. 15 is a block diagram illustrating a method 400 of mating a fluidic cartridge to a system base in accordance with an embodiment. The method 400 (and other methods described herein) may utilize the devices, components, and elements described in the present application. The method 400 may include providing, at 402, a system base. The system base is configured to receive one or more liquids to perform a designated assay, such as nucleic acid sequence or, more specifically, an SBS protocol. The system base may be a base instrument that includes the devices necessary for performing the designated assay, such as a detection assembly. In other embodiments, the system base may be an intermediate component that is positioned between fluidic cartridge and the instrument. For example, the system base may be a manifold. In particular embodiments, the system base is similar to the system base 102 (FIG. 1), the system base 320 (FIG. 9), or the system base 378 (FIG. 13).

The method 400 also includes providing, at 404, a fluidic cartridge. The fluidic cartridges includes one or more liquids that may be deliver to the system base. Optionally, the providing operation at 404 includes providing more than one fluidic cartridge for a single system base. As described herein, the fluidic cartridge may include a transfer tube having a distal end in which the distal end has a fluidic port that is in flow communication with a reservoir of the fluidic cartridge. The fluidic cartridge may also include a movable seal that is positioned to block flow of the liquid through the fluidic port. The fluidic cartridge may be similar to, for example, the fluidic cartridge 200 (FIG. 2). The transfer tube may be similar to the transfer tube 242 (FIG. 4), and the movable seal may be similar to the movable seal 222 or 223 (FIG. 2).

The method 400 may also include mating, at 406, the fluidic cartridge and the system base. In certain embodiments, the mating operation may include loading the fluidic cartridge onto the system base. For example, the mating side of the fluidic cartridge may face a top side of the system base in a direction that is along a gravitational force direction. Access openings of corresponding socket chambers of the fluidic cartridge may be aligned with corresponding projections of the system base. As the mating side is loaded onto the top side of the system base, the projections may displace the movable seals within the socket chambers. The piercing segments of the transfer tubes may pierce the movable seals such that fluidic ports of the piercing segments clear the movable seals.

When the fluidic cartridge is loaded by an operator (e.g., user or machine), the force generated by the operator be sufficient to overcome any frictional forces generated by the movable seals. More specifically, the movable seals may be held at the closed positions by frictional forces between the movable seals and inner surfaces of the socket chamber. As the fluidic cartridge is loaded, the frictional forces may be overcome such that the movable seals are moved to the displaced positions.

In other embodiments, the mating operation, at 406, may include moving the system base (or a portion thereof) while the fluidic cartridge remains stationary. Alternatively, both the fluidic cartridge and the system base may be moved relative to each other. For example, the base projection may be movable with respect to the system base (e.g., attached to an end of a tube) and inserted into the socket chamber causing the movable seal to be displaced.

After the mating operation, liquid may be permitted to flow through the fluidic port after the fluidic port clears the movable seal. Optionally, the method 400 may include flowing, at 408, the liquid through the transfer tube of the fluidic cartridge to the fluidic port of the system base. The flowing may be facilitated by one or more pumps and/or one or more vents in flow communication with the reservoir. For example, the system base may include a pump that draws the liquid through the transfer tube and into the system base. Optionally, the method 400 may include performing, at 410, a designated assay protocol using the liquid of the fluidic cartridge. In particular embodiments, the designated assay protocol is nucleic acid sequencing.

FIG. 16 is a block diagram illustrating a method 420 of assembling a fluidic cartridge in accordance with an embodiment. Like the method 400 (FIG. 15), the method 420 may utilize various structures described herein. For example, the method 420 may include providing, at 422, a cartridge housing, such as the cartridge housing 201 (FIG. 2). The cartridge housing may be coupled to a transfer tube, such as the transfer tube 242 (FIG. 4). In some embodiments, the cartridge housing is an integral structure that defines exterior walls of the cartridge housing and one or more liquid containers. In other embodiments, the cartridge housing may be separately coupled to the liquid containers. The transfer tube may have a distal end that includes a fluidic port that is in flow communication with a reservoir.

The method 420 may also include positioning, 424, a movable seal to block the fluidic port. The movable seal may be similar to the movable seal 222 or the movable seal 223. In particular embodiments, the cartridge housing has a mating side that includes one or more access openings. Each of the access openings may be an opening to a socket chamber. Each movable seal may be positioned within a corresponding socket chamber such that the movable seal engages the transfer tube and blocks flow through the fluidic port. The movable seal may be initially positioned in a closed position. However, the movable seal may be permitted to slide along the transfer tube from a closed position to a displaced position during a mating operation as described above.

Optionally, the method 420 may include filling, at 426, the reservoir(s) with corresponding liquid(s). The number and types of liquids may be based on the particular assay protocol that the fluidic cartridge is intended for. For example, sequencing protocols may include a wash solution, nucleotides solution, cleaving solution, buffer solution, etc. If the reservoirs have open ends, the reservoirs may be sealed, at 427, to hold the corresponding liquids therein. The volumes provided may be based on the expected volume to be used during the assay protocol. Optionally, the fluidic cartridge may be frozen, at 428, and prepared for shipping and/or storing, at 430.

FIG. 17 is a block diagram illustrating a method 440 of re-furbishing a used fluidic cartridge in accordance with an embodiment. The method 440 may include receiving, at 442, a used fluidic cartridge. The used fluidic cartridge may include a cartridge housing having one or more liquid containers and transfer tubes that were previously used to supply liquids to a system. The transfer tubes may be coupled to the liquid containers. The transfer tubes may be operably coupled to used movable seals. The used movable seals may be damage (e.g., pierced) by the transfer tubes.

At 444, the used movable seals may be removed. Optionally, at 446, the cartridge housing may be cleaned and/or sterilized. At 448, the method 440 may include positioning new movable seals to block the fluidic ports of the transfer tubes. The positioning may include embedding distal ends of the transfer tubes into the corresponding new movable seals. Optionally, the method 440 may include de-coupling the used transfer tubes with respect to the liquid containers and coupling new transfer tubes to the liquid containers. New movable seals may then be applied to the new transfer tubes. The term "new," when used with respect to movable seals, may include unused movable seals or include seals that have been repaired and/or cleaned such that the movable seals may be used again. At 450, liquid(s) may be provided to the corresponding reservoir(s).

Figure 18:
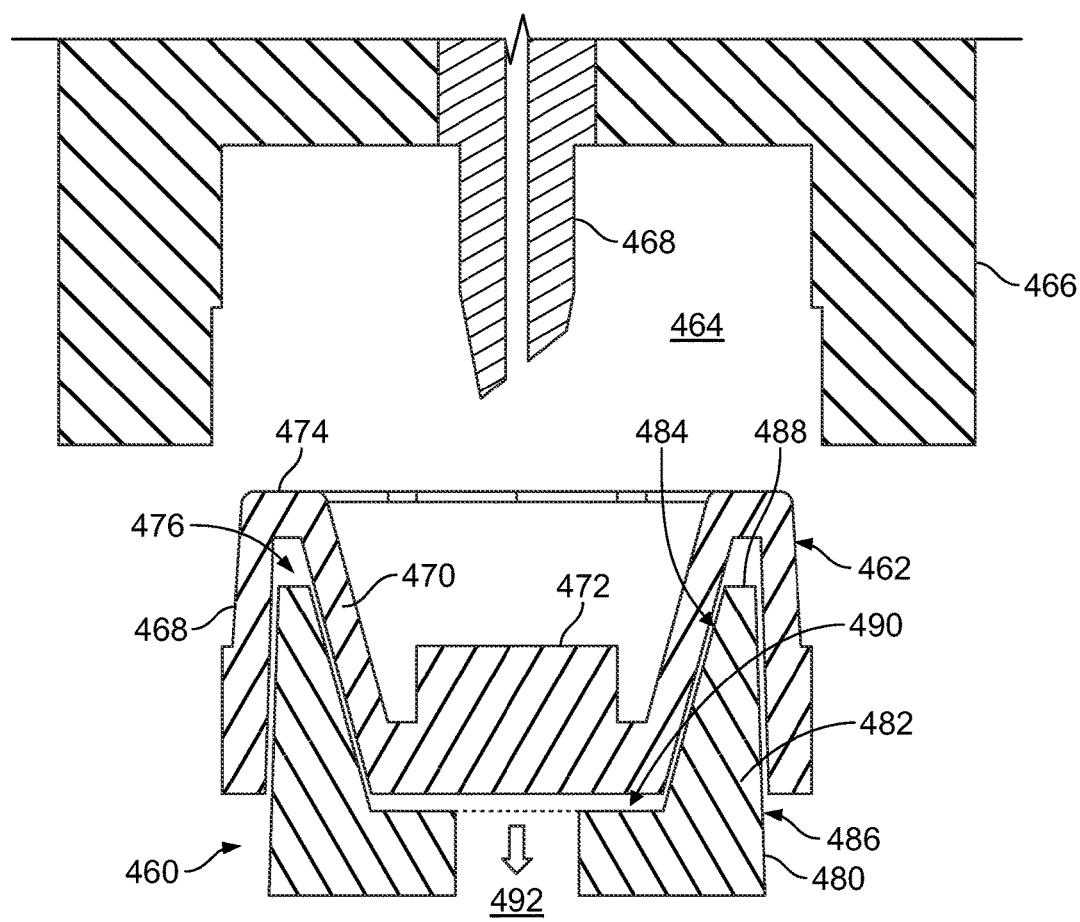
FIG. 18 is a partial cross-section illustrating a positioning tool for installation of a movable seal.

FIG. 18 illustrates a positioning tool 460 that may be used for positioning a movable seal 462 within a socket chamber 464 of a cartridge housing 466. For example, the positioning tool 460 may be used to perform the positioning, at 448 (FIG. 17). The cartridge housing 466 may be similar or identical to the cartridge housing 101 (FIG. 1) or the cartridge housing 201 (FIG. 2). As shown, a transfer tube 468 is secured to the cartridge housing 466 and is disposed within the socket chamber 464. The socket chamber 464 opens to an exterior of the cartridge housing 466 and is configured to receive the movable seal 462.

The positioning tool 460 may be configured to hold the movable seal 462 while positioning the movable seal 462 within the socket chamber 464 and release the movable seal 462 after the movable seal 462 is operably positioned within the socket chamber 464. The movable seal 462 is similar or identical to the movable seal 223 (FIG. 3) and includes a securing wall 468, an elastic wall 470, and a seal membrane 472. The movable seal 462 also includes a wall rim 474 that joins the securing and elastic walls 468, 470. A radial space 476 is defined between the elastic wall 470 and the securing wall 468.

The positioning tool 460 includes a tool housing 480 having a positioning wall 482. The positioning wall 482 includes an inner housing surface 484 and an outer housing surface 486. A leading surface or edge 488 joins the inner and outer housing surfaces 484, 486. The positioning wall 484 is sized and shaped relative to the radial space 476 of the movable seal 462 so that the positioning wall 482 may be inserted into the radial space 476.

The inner housing surface 484 defines a seal-receiving space 490. The seal-receiving space 490 may be sized and shaped relative to the movable seal 462 so that the positioning tool 460 may hold the movable seal 462 therein. For example, in the illustrated embodiment, the seal-receiving space 490 is sized and shaped relative to the elastic wall 470 and the seal membrane 472. In some embodiments, an interference fit may be formed between the inner housing surface 484 and at least one of the elastic wall 470 or the seal membrane 472. Frictional forces generated by the interference fit may be sufficient for temporarily holding the movable seal 462 while positioning the movable seal 462 within the socket chamber 464, but may also allow the movable seal 462 to be released from the positioning tool 460 when the positioning tool 460 is withdrawn from the socket chamber 464 after the loading process.

Optionally, the tool housing 480 may include a flow passage 492 that is in flow communication with a vacuum source (not shown). In some embodiments, the vacuum source is configured to generate a negative pressure that pulls the seal membrane 472 toward the flow passage 492 and holds the movable seal 462 against the tool housing 480. As such, the vacuum source may hold the movable seal 462 with respect to the tool housing 480 as the movable seal 462 is positioned within the socket chamber 464. After the movable seal 462 is positioned within the socket chamber 464, the negative pressure may be cut off or a positive pressure may be provided thereby releasing the movable seal 462 with respect to the positioning tool 460.

In some circumstances, the seal membrane 472 may move laterally within the socket chamber 464 as the transfer tube 468 pierces the seal membrane 472. The positioning tool 460 is configured to impede such movement. More specifically, the inner housing surface 484 may engage the elastic wall 470 and/or the seal membrane 472 and block the seal membrane 472 from moving in a direction that is transverse to the insertion direction.

In an embodiment, a fluidic cartridge is provided that includes a liquid container having a reservoir configured to hold a liquid. The liquid container includes an interior surface. The fluidic cartridge also includes a transfer tube extending from the interior surface to a distal end. The distal end includes a fluidic port that is in flow communication with the reservoir through the transfer tube. The transfer tube has a piercing segment that includes the distal end. The fluidic cartridge also includes a movable seal that is engaged to the piercing segment of the transfer tube and configured to slide along the piercing segment from a closed position to a displaced position during a mating operation between the fluidic cartridge and a system base. The movable seal blocks flow of the liquid through the fluidic port when in the closed position. The piercing segment extends through the movable seal when in the displaced position such that the fluidic port clears the movable seal and the liquid is permitted to flow through the fluidic port.

In one aspect, the movable seal of the fluidic cartridge may include an inner side that faces the interior surface of the liquid container and an outer side that is configured to engage the system base. The inner side of the movable seal and the interior surface of the liquid container may have an operative gap therebetween when the movable seal is in the closed position. The inner side may move closer to the interior surface as the movable seal moves to the displaced position.

In another aspect, the fluidic cartridge may include a cartridge housing that is coupled to the liquid container. The cartridge housing may have an external mating side that is configured to interface with the system base during the mating operation. The mating side may include an access opening that permits the system base to engage the movable seal during the mating operation.

In another aspect, the fluidic cartridge may include a cartridge housing that is coupled to the liquid container. The cartridge housing may define a socket chamber that opens to an exterior of the cartridge housing. The transfer tube and the movable seal may be disposed within the socket chamber.

In another aspect, the movable seal may include a seal membrane that engages the piercing segment of the transfer tube and an elastic wall that extends from the seal membrane and toward the interior surface of the liquid container. The elastic wall may hold the seal membrane in the closed position and permit the seal membrane to be moved to the displaced position. Optionally, the elastic wall may be flexed between the interior surface of the liquid container and the seal membrane when the movable seal is in the displaced position. Also optionally, the fluidic cartridge may include a cartridge housing that is coupled to the liquid container. The movable seal may also include a securing wall that is attached to the seal membrane and the elastic wall. The securing wall may couple the seal membrane and the elastic wall to the cartridge housing. The securing wall may have a substantially fixed position as the seal membrane is moved from the closed position to the displaced position.

In another aspect, the fluidic cartridge may include a cartridge housing that has a plurality of the liquid containers, a plurality of the transfer tubes, and a plurality of the movable seals.

In another aspect, the transfer tube and the liquid container may be formed from a common mold.

In another aspect, the transfer tube and the liquid container may be discrete elements that are coupled to each other.

In another aspect, the distal end may be embedded within the movable seal when in the closed position.

In another aspect, the movable seal is disc-shaped.

In another aspect, the movable seal may include a seal membrane having inner and outer side surfaces that face in opposite directions. The movable seal may have a uniform thickness measured between the inner and outer side surface.

In an embodiment, a method is provided that includes providing a system base configured to receive a liquid for a designated assay and providing a fluidic cartridge that includes a transfer tube having a distal end. The distal end includes a fluidic port that is in flow communication with a reservoir of the fluidic cartridge through the transfer tube. The reservoir includes the liquid. The fluidic cartridge also includes a movable seal that is positioned to block flow of the liquid through the fluidic port. The method may also include mating the fluidic cartridge and the system base. The movable seal is displaced by the system base as the fluidic cartridge is mated with the system base such that the movable seal slides along the transfer tube and the fluidic port clears the movable seal. The liquid is permitted to flow through the fluidic port after the fluidic port clears the movable seal.

In one aspect, mating the fluidic cartridge and the system base may include moving the fluidic cartridge along a loading axis. The movable seal may slide in a direction that is parallel to the loading axis.

In another aspect, the fluidic cartridge may include a cartridge housing that includes the reservoir. The movable seal may move relative to the cartridge housing during the mating operation, wherein an operative gap exists between the movable seal and the cartridge housing prior to the mating operation. The movable seal may move closer to the cartridge housing as the movable seal is displaced.

In another aspect, the fluidic cartridge may include a cartridge housing that holds the movable seal. The cartridge housing may have an external mating side that includes an access opening. The system base may include a base projection that extends through the access opening and engages the movable seal during the mating operation.

In another aspect, the base projection includes a fluidic port of the system base, wherein the fluidic port of the system base and the fluidic port of the transfer tube are fluidically coupled after the mating operation.

In another aspect, the method may also include flowing the liquid through the transfer tube of the fluidic cartridge to the fluidic port of the system base.

Optionally, the method may also include performing a designated assay protocol using the liquid of the fluidic cartridge.

In another aspect, the fluidic cartridge may include a cartridge housing that defines a socket chamber that opens to an exterior of the cartridge housing. The transfer tube extends into socket chamber and the movable seal is disposed within the socket chamber. The system base includes a base projection that extends into the socket chamber and engages the movable seal during the mating operation.

In another aspect, the movable seal includes a seal membrane that engages the transfer tube and an elastic wall that holds the seal membrane in the closed position and permits the seal membrane to be moved to the displaced position. Optionally, the elastic wall may be flexed when the seal membrane is in the displaced position.

In another aspect, the fluidic cartridge may include a cartridge housing that includes a plurality of the liquid containers, a plurality of the transfer tubes, and a plurality of the movable seals.

In an embodiment, a method of assembling a fluidic cartridge is provided. The method includes providing a cartridge housing and a transfer tube that is coupled to the cartridge housing and has a distal end. The distal end includes a fluidic port that is in flow communication with a reservoir through the transfer tube. The method may also include positioning a movable seal to block the fluidic port. The movable seal is configured to slide along the transfer tube from a closed position to a displaced position during a mating operation. The movable seal blocks flow of a liquid through the fluidic port when in the closed position. The transfer tube is configured to extend through the movable seal when in the displaced position such that the fluidic port clears the movable seal and the liquid is permitted to flow through the fluidic port.

In one aspect, the cartridge housing may include a liquid container having the reservoir that is configured to hold the liquid. The liquid container and the transfer tube may be molded from a common material.

In another aspect, the liquid container and the transfer tube may be discrete elements coupled to each other.

In another aspect, the cartridge housing may include a socket chamber that opens to an exterior of the cartridge housing. The transfer tube may extend into the socket chamber, wherein positioning a movable seal to block the fluidic port may include positioning the movable seal within the socket chamber.

In another aspect, positioning the movable seal to block the fluidic port may include coupling the movable seal to the cartridge housing such that the movable seal is not inadvertently removed from the socket chamber.

In another aspect, the method includes filling the reservoir with the liquid.

In another aspect, the method includes freezing the cartridge housing and at least one of shipping the cartridge housing or storing the cartridge housing.

In another aspect, the method includes mating the cartridge housing with a system base. The movable seal may be displaced by the system base as the fluidic cartridge is mated with the system base such that the movable seal slides along the transfer tube and the fluidic port clears the movable seal. The liquid may be permitted to flow through the fluidic port after the fluidic port clears the movable seal.

In an embodiment, a method of re-furbishing a fluidic cartridge is provided that includes receiving a fluidic cartridge having a cartridge housing that includes a liquid container and a transfer tube coupled to the liquid container. The transfer tube has a distal end that includes a fluidic port that is in flow communication with a reservoir of the liquid container through the transfer tube. The method may also include removing a used seal that is engaged to the transfer tube and positioning a movable seal to block the fluidic port. The movable seal is configured to slide along the transfer tube from a closed position to a displaced position during a mating operation. The movable seal blocks flow of the liquid through the fluidic port when in the closed position. The transfer tube may be configured to extend through the movable seal when in the displaced position such that the fluidic port clears the movable seal and the liquid is permitted to flow through the fluidic port. The method also includes providing a liquid into the reservoir.

In an aspect, the method also includes de-coupling a used tube with respect to the liquid container and coupling the transfer tube to the liquid container.

In another aspect, the method also includes sterilizing the liquid container prior to providing the liquid into the reservoir.

In an embodiment, a system is provided that includes a system base configured to conduct an assay protocol with a liquid and a fluidic cartridge that is configured to engage the system base. The fluidic cartridge includes a liquid container having a reservoir configured to hold the liquid. The liquid container may include an interior surface. The fluidic cartridge also includes a transfer tube extending from the interior surface to a distal end. The distal end includes a fluidic port that is in flow communication with the reservoir through the transfer tube. The transfer tube has a piercing segment that includes the distal end. The fluidic cartridge also includes a movable seal that is engaged to the piercing segment of the transfer tube and configured to slide along the piercing segment from a closed position to a displaced position when the fluidic cartridge is mated with the system base. The movable seal blocks flow of the liquid through the fluidic port when in the closed position. The piercing segment extends through the movable seal when in the displaced position such that the fluidic port clears the movable seal and the liquid is permitted to flow through the fluidic port into the system base.

In an aspect, the system base may include a sensor that is configured to detect designated reactions.

In another aspect, the movable seal may include an inner side that faces the liquid container and an outer side that is configured to engage the system base. The inner side of the movable seal and the liquid container may have an operative gap therebetween when the movable seal is in the closed position. The inner side may move closer to the liquid container as the movable seal moves to the displaced position.

In another aspect, the fluidic cartridge may include a cartridge housing that is coupled to the liquid container. The cartridge housing may have an external mating side that is configured to interface with the system base during the mating operation. The mating side may also include an access opening that permits the system base to engage the movable seal during the mating operation.

In another aspect, the fluidic cartridge may include a cartridge housing that is coupled to the liquid container. The cartridge housing may define a socket chamber that opens to an exterior of the cartridge housing. The transfer tube may extend into socket chamber and the movable seal being may be disposed within the socket chamber.

In another aspect, the movable seal may include a seal membrane that engages the piercing segment of the transfer tube and an elastic wall that extends from the seal membrane and toward the interior surface of the liquid container. The elastic wall may hold the seal membrane in the closed position and permit the seal membrane to be moved to the displaced position.

Optionally, the fluidic cartridge may include a cartridge housing that is coupled to the liquid container. The movable seal may also include a securing wall that is attached to the seal membrane and the elastic wall. The securing wall may couple the seal membrane and the elastic wall to the cartridge housing. The securing wall may have a substantially fixed position as the seal membrane is moved from the closed position to the displaced position.

In another aspect, the fluidic cartridge may include a cartridge housing that includes a plurality of the liquid containers, a plurality of the transfer tubes, and a plurality of the movable seals.

In another aspect, the liquid container and the transfer tube are formed from a common mold.

In another aspect, the liquid container and the transfer tube may be discrete elements coupled to each other.

In another aspect, the system base may be configured to perform nucleic acid sequencing.

In another aspect, the system base may be configured to execute a sequencing-by-synthesis (SBS) protocol.

In another aspect, the liquid container may be configured to hold a non-polar liquid and the system base may be configured to perform electrowetting of polar droplets using the non-polar liquid.

In another aspect, the fluidic cartridge may include a cartridge housing that includes a plurality of the liquid containers, a plurality of the transfer tubes, and a plurality of the movable seals. At least one of the liquid containers may be configured to hold a polar liquid and at least one of the liquid containers is configured to hold a non-polar liquid. The system base may be configured to perform electrowetting operations using the polar and non-polar liquids.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements whether or not they have that property.

It should be noted that the particular arrangement of components (e.g., the number, types, placement, or the like) of the illustrated embodiments may be modified in various alternative embodiments. In various embodiments, different numbers of a given element (e.g., component, assembly, module, etc.) may be employed, a different type or types of a given element may be employed, a given element may be added, or a given element may be omitted.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The patentable scope should, therefore, be determined with reference to the appended claims, along with the full scope of equivalents to which such claims are entitled.

As used in the description, the phrase "in an exemplary embodiment" and the like means that the described embodiment is just one example. The phrase is not intended to limit the inventive subject matter to that embodiment. Other embodiments of the inventive subject matter may not include the recited feature or structure. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112(f), unless and until such claim limitations expressly use the phrase "means for" followed by a statement of function void of further structure.

The following claims recite one or more embodiments of the present application and are hereby incorporated into the description of the present application.

What is claimed is:

1. A fluidic cartridge comprising:
   a liquid container having a reservoir configured to hold a liquid, the liquid container including an interior surface;
   a transfer tube extending from the interior surface to a distal end, the distal end including a fluidic port that is in flow communication with the reservoir through the transfer tube, the transfer tube having a piercing segment that includes the distal end; and
   a movable seal engaged to the piercing segment of the transfer tube and configured to slide along the piercing segment from a closed position to a displaced position during a mating operation between the fluidic cartridge and a system base, the movable seal blocking flow of the liquid through the fluidic port when in the closed position, the piercing segment extending through the movable seal when in the displaced position such that the fluidic port clears the movable seal and the liquid is permitted to flow through the fluidic port.

2. The fluidic cartridge of claim 1, wherein the movable seal includes an inner side that faces the interior surface of the liquid container and an outer side that is configured to engage the system base, the inner side of the movable seal and the interior surface of the liquid container having an operative gap therebetween when the movable seal is in the closed position, the inner side moving closer to the interior surface as the movable seal moves to the displaced position.

3. The fluidic cartridge of claim 1, wherein the fluidic cartridge comprises a cartridge housing that is coupled to the liquid container, the cartridge housing having an external mating side that is configured to interface with the system base during the mating operation, the mating side including an access opening that permits the system base to engage the movable seal during the mating operation.

4. The fluidic cartridge of claim 1, wherein the fluidic cartridge comprises a cartridge housing that is coupled to the liquid container, the cartridge housing defining a socket chamber that opens to an exterior of the cartridge housing, the transfer tube and the movable seal being disposed within the socket chamber.

5. The fluidic cartridge of claim 1, wherein the movable seal includes a seal membrane that engages the piercing segment of the transfer tube and an elastic wall that extends from the seal membrane and toward the interior surface of the liquid container, the elastic wall holding the seal membrane in the closed position and permitting the seal membrane to be moved to the displaced position.

6. The fluidic cartridge of claim 5, wherein the elastic wall is flexed between the interior surface of the liquid container and the seal membrane when the movable seal is in the displaced position.

7. The fluidic cartridge of claim 5, wherein the fluidic cartridge includes a cartridge housing that is coupled to the liquid container, the movable seal also including a securing wall that is attached to the seal membrane and the elastic wall, the securing wall coupling the seal membrane and the elastic wall to the cartridge housing, the securing wall having a substantially fixed position as the seal membrane is moved from the closed position to the displaced position.

8. The fluidic cartridge of claim 1, wherein the fluidic cartridge includes a cartridge housing that includes a plurality of the liquid containers, a plurality of the transfer tubes, and a plurality of the movable seals.

9. The fluidic cartridge of claim 1, wherein the transfer tube and the liquid container are formed from a common mold.

10. The fluidic cartridge of claim 1, wherein the transfer tube and the liquid container are discrete elements coupled to each other.

11. The fluidic cartridge of claim 1, wherein the distal end is embedded within the movable seal when in the closed position.

12. The fluidic cartridge of claim 1, wherein the movable seal includes a seal membrane having inner and outer side surfaces that face in opposite directions, the movable seal having a uniform thickness measured between the inner and outer side surfaces.

13. A method comprising:
providing a system base configured to receive a liquid for a designated assay;
providing a fluidic cartridge that includes a transfer tube having a distal end, the distal end including a fluidic port that is in flow communication with a reservoir of the fluidic cartridge through the transfer tube, the reservoir including the liquid, the fluidic cartridge also including a movable seal that is positioned to block flow of the liquid through the fluidic port; and
mating the fluidic cartridge and the system base, the movable seal being displaced by the system base as the fluidic cartridge is mated with the system base such that the movable seal slides along the transfer tube and the fluidic port clears the movable seal, wherein the liquid is permitted to flow through the fluidic port after the fluidic port clears the movable seal.

14. The method of claim 13, wherein mating the fluidic cartridge and the system base includes moving the fluidic cartridge along a loading axis, the movable seal sliding in a direction that is parallel to the loading axis.

15. The method of claim 13, wherein the fluidic cartridge includes a cartridge housing that includes the reservoir, the movable seal moving relative to the cartridge housing during the mating operation, wherein an operative gap exists between the movable seal and the cartridge housing prior to the mating operation, the movable seal moving closer to the cartridge housing as the movable seal is displaced.

16. The method of claim 13, wherein the fluidic cartridge comprises a cartridge housing that holds the movable seal, the cartridge housing having an external mating side that includes an access opening, the system base including a base projection that extends through the access opening and engages the movable seal during the mating operation.

17. The method of claim 16, wherein the base projection includes a fluidic port of the system base, wherein the fluidic port of the system base and the fluidic port of the transfer tube are fluidically coupled after the mating operation.

18. The method of claim 17, further comprising flowing the liquid through the transfer tube of the fluidic cartridge to the fluidic port of the system base.

19. The method of claim 18, further comprising performing a designated assay protocol using the liquid of the fluidic cartridge.

* * * * *